(12) United States Patent
Goel

(10) Patent No.: US 7,893,289 B2
(45) Date of Patent: Feb. 22, 2011

(54) ADAMANTANAMINES AND NERAMEXANE SALTS OF THIOMOLYBDIC AND THIOTUNGSTIC ACIDS

(75) Inventor: Om P. Goel, Ann Arbor, MI (US)

(73) Assignee: SSV Therapeutics, Inc., Ann Arbor, MI (US)

( * ) Notice: Subject to any disclaimer, the term of this patent is extended or adjusted under 35 U.S.C. 154(b) by 442 days.

(21) Appl. No.: 11/992,991

(22) PCT Filed: Feb. 21, 2008

(86) PCT No.: PCT/US2008/002308

§ 371 (c)(1),
(2), (4) Date: Apr. 2, 2008

(87) PCT Pub. No.: WO2008/103421

PCT Pub. Date: Aug. 28, 2008

(65) Prior Publication Data

US 2010/0216775 A1    Aug. 26, 2010

Related U.S. Application Data

(60) Provisional application No. 60/902,476, filed on Feb. 21, 2007, provisional application No. 60/993,131, filed on Sep. 10, 2007.

(51) Int. Cl.
*C07F 11/00* (2006.01)
*A61K 31/28* (2006.01)

(52) U.S. Cl. .............................. 556/57; 514/492; 546/8

(58) Field of Classification Search ............... 556/57; 546/8; 514/492
See application file for complete search history.

(56) References Cited

U.S. PATENT DOCUMENTS 6,828,462 B2    12/2004  Henrich et al.
(Continued)

FOREIGN PATENT DOCUMENTS

WO    WO/2005/058293    6/2005
(Continued)

OTHER PUBLICATIONS

John Hardy et al., "The Amyloid Hypothesis of Alzheimer's Disease: Progress and Problems on the Road to Therapeutics", Science 297, 353-356 (2002).
(Continued)

*Primary Examiner*—Porfirio Nazario Gonzalez
(74) *Attorney, Agent, or Firm*—Technology Law, PLLC; Karen L. Kimble

(57) ABSTRACT

This invention concerns adamantanamines (e.g. memantine, amantadine, and rimantadine) and neramexane salts of thiomolybdic and thiotungstic acids, including their preparation and pharmaceutical compositions, as dual acting drugs. These salts are used to treat or potentially arrest the neurodegenerative pathophysiology, clinical signs and symptoms of dementia of the Alzheimer's type, Parkinson's, Huntington's, AIDS-related dementia and Schizophrenia and its cognitive deficits. Additional uses of these derivatives include antiviral activity. The novel compositions of the present invention appear particularly useful in enhancing the therapeutic benefits of copper-sequestering tetrathiomolybdates in treating elevated copper-induced toxicities in neurologically presenting Wilson's disease, and in treating diseases of the inflammatory etiology and abnormal copper biochemistry, such as tumor angiogenesis, liver cirrhosis, hepatitis, pulmonary fibrosis and other fibrotic diseases, cardiovascular disease, cerebral ischemia, renal anemia, rheumatoid arthritis, diabetes, obesity, gastrointestinal disorders, and eye diseases such as glaucoma, proliferative diabetic retinopathy, and age related macular degeneration. These compounds have excellent stability and aqueous solubility for good oral bioavailability.

30 Claims, 6 Drawing Sheets

U.S. PATENT DOCUMENTS

| | | |
|---|---|---|
| 6,855,340 B2 | 2/2005 | Brewer |
| 7,145,037 B2 | 12/2006 | Makovec et al. |
| 7,189,865 B2 | 3/2007 | Ternansky et al. |
| 2004/0019087 A1 | 1/2004 | Ternansky et al. |
| 2004/0259945 A1 | 12/2004 | Brewer et al. |
| 2006/0160805 A1 | 7/2006 | Ternansky et al. |

FOREIGN PATENT DOCUMENTS

| | | |
|---|---|---|
| WO | WO/2007/117544 | 10/2007 |

OTHER PUBLICATIONS

Stuart A. Lipton et al., "Excitatory Amino Acids as a Final Common Pathway for Neurologic Disorders", N. Engl. J. of Med. 330(9), 613-622 (1994).

Mihaela Necula et al., J. Biol. Chem. 282(14), 10311-10324 (2007).

F. G. De Felice et al., "Alzheimer's Disease-type Neuronal tau Hyperposphorylation Induced by AB Oligomers", Neurobiol. Aging in press 2007, pub. Elsevier.

J. P. Mothet et al., "A Critical Role for the Glial-derived Neuromodulator D-serine in the Age-related Deficits of Cellular Mechanisms of Learn..." Aging Cell 5, 267-274 (2006).

H. Hsieh et al., "AMPAR Removal Underlies AB-Induced Synaptic Depression and Dendritic Spine Loss", Neuron 52, 831-843 (2006), pub. Elsevier.

E. M. Snyder et al., "Regulation of NMDA Receptor Trafficking by Amyloid-B", Nature Neurosci. 8(8); 1051-1058 (2005).

C. Haass et al., "Soluble Protein Oligomers in Neurodegeneration: Lessons from the Alzheimer's Amyloid B-peptide", Nat. Rev. Mol. Cell Biol. 8(2), 101-112 (2007), pub. Nature.

G.L. Wenk et al., "Potential Role of N-methyl-D aspartate Receptors as Executors of Neurodegeneration Resulting from . . . ", Behavioural Pharrn. 17(5&6), 411-424 (2006).

D. Van Dam et al., "Cognitive Evaluation of Disease-modifying Efficacy of Galantamine and Memantine in the APP23 Model", Eur. Neuropsychopharm. 16, 59-69 (2006).

P. O'Suilleabhain, MD et al., "A Randomized Trial of Amantadine in Huntington Disease", Arch. Neurol. 60(7), 996-998 (2003).

D. L. Sparks et at., "Trace Amounts of Copper in Water Induce B-amyloid Plaques and Learning Deficits in a Rabbit Model of Alzheimer's Disease",PNAS 100(19), 11065-11069(2003).

X. Zhu et al., "Alzheimer Disease, the Two-hit Hypothesis: an Update", Biochim. Biophysica Acta 1772, 494-502 (2007).

R. Squitti et al., "Elevation of Serum Copper Levels in Alzheimer's Disease", Neurology 59, 1153-1161 (2002).

R. Squitti et al., "Excess of Serum Copper not Related to Ceruloplasmin in Alzheimer Disease", Neurology 64(6), 1040-1046 (2005).

R. Squitti et al., "Excess of Nonceruloplasmin Serum Copper and Ad Correlates with MMSE, CSF B-amyloid and h-tau", Neurology 67(1), 76-82 (2006).

L. Rossi et al., "Alteration of Peripheral Markers of Copper Homeostasis in Alzheimer's Disease Patients: . . . ", J. Nutrition, Health & Aging 11, 408-417 (2007).

A. I. Bush, "Metals and Neuroscience", Curr. Opinion in Chem. Biol. 4(2), 184-191 (2000).

A.R. White et al.,"Degration of the Alzheimer Disease Amyloid B-peptide by Metal-dependent Up-regulation of Metalloprotease Activity", J. Biol. Chem.281(26), 17670-17680(2006).

G. J. Brewer et al., "treatment of Wilson Disease with Ammonium Tetrathiomolybdate", Arch. Neurol. 63(4), 521-527 (2006).

J.F. Quinn et al.,"Copper Complexing with Tetrathiomolybdate in a Transgenic Mouse Model of Alzheimer's Disease", abst.Soc. for Neuroscience 37th Ann.Meeting, San Diego 2007.

B.R. Srinivasan et al., "Synthesis, Crystal Structures and Properties of Three New Tetrathiomolybdates ", Zeitschrift fuer Naturforschung,B:Chem. Sci. 59(10), 1083-1092 (2004).

ADAMANTANAMINES AND NERAMEXANE SALTS OF THIOMOLYBDIC AND THIOTUNGSTIC ACIDS

FIELD OF THE INVENTION

The present invention concerns the preparation and uses of adamantanamines (e.g. memantine, amantadine and rimantadine) and neramexane(s) salts of thiomolybdic acids and thiotungstic acids. Their pharmaceutical compositions incorporate two complementary, bioavailable pharmacophores, which are useful in treating and arresting progression of neurodegenerative diseases such as dementia of Alzheimer's, Huntington's and Parkinson's diseases, and diseases of the eye such as glaucoma, age related macular degeneration, and diabetic retinopathy.

BACKGROUND OF THE INVENTION

Alzheimer's disease (AD) is a progressive, neurodegenerative illness characterized by, but not limited to, the aggregation, and deposition of β-amyloid (Aβ) protein plaques in the neocortex, (e.g., J. Hardy and D. Selkoe, Science, 297, 353-356 (2002), and from abnormal activation of the glutamatergic N-methyl-D-aspartate receptors (NMDARs) [e.g., D. Choi, Neuron, 1(8), 623-634, (1988); and S. Lipton et al., New England Journal of Medicine, 330(9), 613-622 (1994)]. Plaques form when the normally occurring, trans-membrane amyloid precursor protein (APP) is broken down into peptide fragments and folded into dense deposits that impair neuronal functioning and eventually results in cellular death. The biochemical research has focused on finding drugs that would dissolve existing plaques or stop new ones from forming. Based on recent studies, formation and aggregation of soluble Aβ (1-42) oligomers are postulated to be a causative factor in the decline of cognitive function, and intervention of this biochemical pathway is a current therapeutic target [e.g., M. Necula et al., J. Biol. Chem., 282, 10311-10324 (2007); and F. De Felice et al., Neurobiol. Aging, in press (2007)].

Residing in the same areas of the brain affected by Aβ plaques are the N-methyl-D-aspartate receptors (NMDARs), which are part of an intricate signaling system involved in many physiological processes, including learning and memory. Upon NMDAR depolarization $Ca^{2+}$ flows into the cell and modulates gene expression through a cascade of signaling mechanisms. Extended activation can cause morphological changes to postsynaptic dendritic spines and facilitate long-term potentiation (LTP), a momentary or long term enhanced synaptic signaling that occurs in learning and memory (e.g., J. Mothet et al., Aging Cell, 5(3), 267-274 (2006). Unmodulated activation of NMDAR (i.e. increased frequency of activation requiring lower concentration of glutamate) impairs the precision needed for neurotransmission, and leads to neurodegeneration. Within the glutamatergic synapse, plaque formation in combination with NMDAR dysfunction amplifies neuronal vulnerabilities [e.g., T. Harkany et al., Eur. J. of Neuroscience, 12(8), 2735-2745 (2000); M. Mattson et al., J. of Neuroscience, 12(2) 376-389 (1992); and H. Hsieh et al., Neuron, 52(5), 831-843 (2006)]. In cultured cortical neurons, Aβ decreased cell surface expression of the NMDAR and reduced NMDA-induced currents (e.g., E. Snyder et al., Nature Neuroscience, 8(8), 1051-1058 (2005). Consistent with these studies, Aβ aggregates impair cognition in AD transgenic mouse models [e.g., C. Haass and D. Selkoe, Nat. Rev. Mol. Cell. Biol., 8(2), 101-112, (2007); and S. Lesne et al., Nature, 440, 352-357, (2006)]. Despite evidence of dual pathology involving both Aβ aggregates and abnormal activation of NMDAR, treatment approaches have historically addressed these issues individually.

To date, the only FDA approved drug for the treatment of moderate to severe AD is memantine, (1-amino-3,5-dimethyladamantane), based on the results of a double blind, placebo controlled study [see B. Reisberg et al., N. Engl. J. Med. 348, 1333-1341 (2003)]. Memantine exerts neuroprotective effects in several models of brain injury in experimental animals [e.g., C. Parsons et al., Neuropharmacology 735-767 (1999); G. Wilcock, Lancet Neurol, 2, 503-505 (2003), G. Wenk et al., Behavioural Pharmacology, 17(5-6), 411-424, 2006)]. Memantine allows normal physiological NMDAR activity, while preventing pathological activation. Cognitive improvement in a transgenic mouse model of AD was noted three weeks after cessation of treatment, suggesting that in addition to providing symptomatic relief, memantine may have other disease-modifying properties as well [e.g., D. Dam et al., European Neuropsychopharmacology, 16(1), 59-69, (2006)].

O. Goel, WO/2007/117544, pub. Oct. 18, 2007, by the present inventor, describes novel carnitine conjugates of adamantanamines (e.g. memantine) and neramexane(s) as dual mechanism drugs for various therapeutic uses, including treating dementia of the Alzheimer's type. Memantine is also currently in clinical trials as an oral therapy for treating glaucoma. Amantadine (1-aminoadamantane) and rimantadine [1-(1-adamantyl)ethanamine], both as hydrochloride salts, are in clinical use as antiviral agents [e.g., P. Aldrich, et al., J. Med. Chem. 14, 535-543 (1972)]. Amantadine hydrochloride (Symmetrel®) is prescribed in the treatment of Parkinson's disease and drug induced extra pyramidal side effects. Amantadine and memantine are also suggested in the treatment of Huntington's disease [e.g., P. O'Suilleabhain et al., Arch. Neurol. 60(7), 996-8 (2003)]. A related substance, neramexane (1,3,3,5,5-pentamethylcyclohexylamine), has been in clinical studies for treating AD.

Alzheimer's research has recently begun to examine the role of copper in Aβ-associated aggregation and toxicity. Studies have shown that $Cu^{2+}$ and Aβ peptides form complexes that induce Aβ aggregation and cause cognitive deficits [e.g., C. Atwood et al., J. of Biological Chem., 273(21), 12817-12826 (1998); J. of Neurochemistry, 75(3), 1219-1233 (2000); L. Sparks and B. Schreurs, PNAS, 100(19), 11065-11069 (2003); and A. Bush et al., Science, 265(5177), 1464-1467 (1994)]. In addition, in vitro and in vivo studies have reported that neurotoxicity seen in AD is, in part, the result of these complexes generating $H_2O_2$ [e.g., X. Huang et al., Biochemistry, 38(24), 7609-7616 (1999); J. of Biological Chem., 274(52), 37111-37116 (1999); and X. Zhu, et al., an update, Biochimica et Biophysica Acta (BBA)-Molecular Basis of Disease, 1772(4), 494-502 (2007)]. Postmortem studies have shown a significant increase in copper levels within neuritic plaques in subjects with AD, which is consistent with findings of oxidative damage in the brain (e.g., M. Lovell et al., J. of the Neurological Sciences, 158(1), 47-52 (1998), and the preceding X. Zhu update)]. Furthermore, higher serum copper levels in AD patients compared to cognitively normal individuals support a role for $Cu^{2+}$ in AD pathophysiology [e.g., R. Squitti et al., Neurology, 59, 1153-1161 (2002); Neurology, 64(6), 1040-1046 (2005); Neurology, 67(1), 76-82 (2006); L. Rossi et al., J Nutr. Health Aging, 11(5), 408-417 (2007)].

Under normal physiological conditions, $Cu^{2+}$ which modulates essential metabolic processes, including neurological function, is present in the brain at potentially toxic levels [e.g., A. Bush, Current Opinion in Chemical Biology, 4(2), 184-191 (2000)]. In the unbound ionic state $Cu^{2+}$ causes oxidative damage, and protective mechanisms exist to regulate cellular levels via chaperone proteins, enzymes, storage proteins, organelles, and vesicles [e.g., E. Harris, *Critical Reviews in Clinical Laboratory Sciences*, 40(5), 547-586 (2003)].

Studies with the antibiotic clioquinol (iodochlorhydroxyquin), which chelates $Cu^{2+}$ have been found to improve cognition in a subset of patients with AD, again suggesting that lowering copper levels has therapeutic benefits in the treatment of AD. The drug decreased deposition of Aβ and released soluble Aβ from preformed deposits both in vitro and in AD transgenic mice (e.g., C. Ritchie et al., *Arch Neurol.,* 60, 1685-1691 (2003); and A. White et al., *J. of Biological Chem.* 281(26), 17670-17680 (2006)].

WO/2005/058293, published Jun. 30, 2005, claims use of memantine for treatment of proliferative retinal diseases such as proliferative diabetic retinopathy. Glutamate causes migration and proliferation of retinal pigment epithelium and/or glial cells. Glutamate antagonists, such as memantine can inhibit this pathology. A number of diseases of the eye such as age related macular degeneration caused by overgrowth of retinal blood vessels, which leak and damage vision, may be treated with anti-copper therapies (US Patent Appln. 20040259945, pub. Dec. 23, 2004).

Free copper is a known stimulant of angiogenesis critical to tumor growth and involved in rheumatoid arthritis [e.g., S. Brem, *Cancer Control*, 6, 5 (1999); A. Nasulewicz et al., *Cell. Mol. Biol. Lett.* 7, 308 (2002); US Patent Appln. 20040259945, pub. Dec. 23, 2004; and U.S. Pat. No. 7,189, 865 (2007)].

G. Brewer in U.S. Pat. No. 6,855,340 (2005) discloses the benefits of copper complexing agents in the prevention and treatment of various inflammatory and fibrotic diseases such as pulmonary fibrosis, acute respiratory distress syndrome, liver cirrhosis and hepatitis C, kidney disease, cystic fibrosis, myocardial fibrosis, Alzheimer's disease, retinal inflammation, tissue transplant rejections, etc.

In the last two decades or more, various molecular compositions of inorganic thiomolybdates have emerged as relatively nontoxic copper-complexing therapeutics as alternatives to classical agents such as penicillamine and trientine. Ammonium tetrathiomolybdate (TM) is a potent $Cu^{2+}$ complexing agent that has been used to bind excess circulating $Cu^{2+}$ in patients with Wilson's disease and awaiting regulatory NDA filing (e.g., U.S. Pat. No. 6,855,340 (2005); and *Arch Neurol.,* 63(4) 521-527). Recently, TM was shown to lower insoluble Aβ levels in transgenic mice (Tg2576) over expressing APP [see T. Wadsworth et al., abstract, *Society for Neuroscience 37th Annual Meeting*, San Diego (2007)].

The success of copper chelating agents, such as clioquinol, in treating and preventing Aβ aggregates, along with evidence of increased levels of circulating copper in AD patients, suggest thiomolybdic acid as a complementary pharmacophore to neuroprotective memantine for treating and arresting AD. While numerous complex polymetallic and hetrometallic (e.g. Fe—Mo) thiomolybdenum compounds are known, simple thiomolybdates are derived by stepwise sulfur exchange of oxygen in molybdic acid $MoO_4^{2-}$ in alkaline media, resulting in intermediate mixed oxathio species which may be isolated with careful control of stochiometry. For practical reasons, it is easier to manufacture the perthiomolybdates, which simply precipitate from alkaline solutions as crystalline solids of well-defined compositions. The diammonium tetrathiomolybdate (TM) may be prepared in this manner. (It is commercially available from Aldrich Chemical Co. of Milwaukee, Wis., US.) However, TM is reportedly unstable under ambient conditions in air and humidity with ~55% loss in activity after 50 days (US Patent Appln. 20040259945, pub. Dec. 23, 2004). To improve shelf life, the ammonium cations in amm.TM have been replaced with numerous hydrophobic polyalkyl (quaternary) ammonium cations potentially offering greater stability for pharmaceutical applications [e.g., US Patent Appln. 20040259945, pub. Dec. 23, 2004; and U.S. Pat. No. 7,189,865 (2007)]. However, these compounds in general, offer no additional pharmacological benefits or safety.

Tungsten, in the same group VIb elements, sits right under molybdenum in the periodic table, and has similar chemical properties. Thiotungstates may also be prepared from tungstic acid by oxygen to sulfur exchange. (Aldrich Chemical Co. of Milwaukee, Wis., US, markets ammonium tetrathiotungstate, and piperidine tetrathiotungstate.) R. Ternansky et al., disclose numerous polyalkylamino thiotungstates in US Patent Appln. 20060160805, pub. Jul. 20, 2006. In contrast to thiomolybdates, the thiotungstates are, however, malodorous and do not lend themselves easily to pharmaceutical applications. No clinical studies with thiotungstates have been found to be reported.

Clearly, a novel treatment that could act in concert with, and/or enhance the effects of memantine or related amines and also addresses plaque formation is of considerable clinical relevance.

BRIEF SUMMARY OF THE INVENTION

This invention provides for incorporating two complementary, synergistic, bioavailable, pharmacophores in one chemical entity while maintaining favorable drug-like physicochemical and pharmacokinetic properties. Thus designing, and incorporating a suitable copper-complexing moiety as a second pharmacophore in concert with an adamantanamine (e.g. memantine) is expected to lead to promising candidates for treating AD and related neurological disorders. Also pharmaceutical compositions of a suitable copper-complexing moiety as a second pharmacophore in concert with a glutamate antagonist (e.g. memantine) area again expected to be good candidates for treating proliferative retinal diseases, and glaucoma. This invention addresses these needs with a dual action drug solution.

The present invention discloses the preparation and uses of admantanamines (e.g. memantine, amantadine, rimantadine) and neramexane(s) salts of thiomolybdic acids and thiotungstic acids. These thiomolybdates are at least dual acting by combining, in one molecular entity, the neuroprotective NMDA antagonist activity of memantine or neramexane(s) with the strong copper-complexing properties of thiomolybdic acids. The resulting stable thiomolybdates and their pharmaceutical compositions are particularly useful in treating and potentially arresting progression of neurodegenerative diseases such as Alzheimer's disease (AD), other dementias such as Parkinson's, Huntington's, and AIDS-related dementia, schizophrenia and its cognitive deficits, viral infections, and neurologically presenting Wilson's disease, angiogenesis during tumor growth, liver cirrhosis, hepatitis, pulmonary fibrosis and other fibrotic diseases, cardiovascular disease, cerebral ischemia, renal anemia, rheumatoid arthritis, diabetes, obesity, gastrointestinal disorders and diseases of the eye such as age related macular degeneration, proliferative diabetic retinopathy, and glaucoma.

It is one purpose of this invention to extend the benefits of neuroprotective adamantanamines (e.g., memantine), and neramexanes by incorporating them as replacements of ammonium cations in amm.TM.

The present invention provides a dual acting compound of Formula (I)

$$Z^+ \cdot M^{2-} \cdot Z^+ \quad \text{Formula (I)}$$

wherein:

$M^{2-}$ is selected from the group consisting of $MoO_3S^{2-}$, $MoO_2S_2^{2-}$, $MoOS_3^{2-}$, $MoS_4^{2-}$, $[Mo_2(S_2)_6]^{2-}$, $[Mo_2S_4(S_2)_2]^{2-}$, $[Mo_2S_4(S_4)_2]^{2-}$, $[Mo_3S(S_2)_6]^{2-}$, $WO_3S^{2-}$, $WO_2S_2^{2-}$, $WOS_3^{2-}$ and $WS_4^{2-}$;

$Z^+$ is joined to $M^{2-}$, as shown by the dot, ionically;

$Z^+$ is independently an organic ammonium moiety with an alicyclic or a polyalicyclic group of the tricyclic adamantane selected from the group as shown by Formulae (A), (B) and (C) or monoalicyclic neramexane type as shown by Formula (D), respectively,

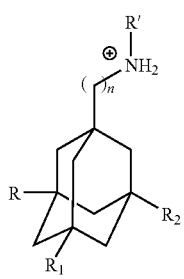

Formula (A)

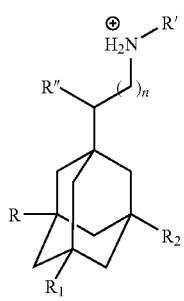

Formula (B)

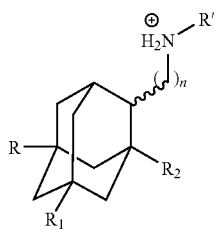

Formula (C)

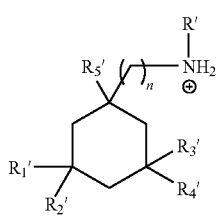

Formula (D)

wherein:

in Formula (A):

R, $R_1$ and $R_2$ are each independently H or $C_1$-$C_6$ straight- or branched-chain alkyl, $C_3$-$C_7$ cycloalkyl (such as cyclopentyl and cyclohexyl), $C_1$-$C_6$ straight- or branched-chain fluoroalkyl (such as fluoromethyl, difluoromethyl, trifluoromethyl, fluoroethyl), $C_2$-$C_6$ alkenyl, $C_2$-$C_6$ alkynyl, alkoxyl, t-butoxycarbonyl, t-butoxycarbonylmethyl, hydroxy, hydroxymethyl, alkoxymethyl, azido, cyano, halo, nitro, trihaloalkyl, $C_1$-$C_6$ mercaptoalkyl, $C_6$-$C_{10}$ aryl [such as phenyl, unsubstituted or substituted with one or more $C_1$-$C_6$ straight- or branched-chain alkyl (such as 3,4-dimethylphenyl), $C_1$-$C_6$ alkoxyl, t-butoxycarbonyl, hydroxy, azido, halo, nitro, trihaloalkyl, or $C_1$-$C_6$ mercaptoalkyl], alkyl($C_6$-$C_{10}$ aryl) (such as a benzyl group, unsubstituted or substituted with one or more $C_1$-$C_6$ straight- or branched-chain alkyl, $C_1$-$C_6$ alkoxyl, 1,3-dioxolanyl, t-butoxycarbonyl, hydroxy, azido, halo or trihaloalkyl), and alkyldiaryl (such as diphenylmethyl, unsubstituted or substituted with one or more $C_1$-$C_6$ straight- or branched-chain alkyl, $C_1$-$C_6$ alkoxyl, 1,3-dioxolanyl, halo or trihaloalkyl);

n=0, 1 or 2; and

R' is H or $C_1$-$C_4$ straight- or branched-chain alkyl, or $C_3$-$C_7$ cycloalkyl (such as cyclopentyl and cyclohexyl); and in Formula (B):

R, $R_1$ and $R_2$ are each independently H or $C_1$-$C_6$ straight- or branched-chain alkyl, $C_3$-$C_7$ cycloalkyl (such as cyclopentyl and cyclohexyl), $C_1$-$C_6$ straight- or branched-chain fluoroalkyl (such as fluoromethyl, difluoromethyl, trifluoromethyl and fluoroethyl), $C_2$-$C_6$ alkenyl, $C_2$-$C_6$ alkynyl, alkoxyl, t-butoxycarbonyl, t-butoxycarbonylmethyl, hydroxy, hydroxymethyl, alkoxymethyl, azido, cyano, halo, nitro, trihaloalkyl, $C_1$-$C_6$ mercaptoalkyl, $C_6$-$C_{10}$ aryl [such as phenyl, unsubstituted or substituted with one or more $C_1$-$C_6$ straight- or branched-chain alkyl (such as 3,4-dimethylphenyl), $C_1$-$C_6$ alkoxyl, t-butoxycarbonyl, hydroxy, azido, halo, nitro, trihaloalkyl or $C_1$-$C_6$ mercaptoalkyl], alkyl ($C_6$-$C_{10}$) aryl [such as a benzyl group unsubstituted or substituted with one or more $C_1$-$C_6$ straight- or branched-chain alkyl, $C_1$-$C_6$ alkoxyl, 1,3-dioxolanyl, t-butoxycarbonyl, hydroxy, azido, halo or trihaloalkyl], and alkyldiaryl (such as diphenylmethyl, unsubstituted or substituted with one or more $C_1$-$C_6$ straight- or branched-chain alkyls, $C_1$-$C_6$ alkoxyl, 1,3-dioxolanyl or trihaloalkyl);

n=0, 1 or 2;

R' is H or $C_1$-$C_4$ straight- or branched-chain alkyl, or $C_3$-$C_7$ cycloalkyl (such as cyclopentyl and cyclohexyl); and R" is $C_1$-$C_4$ straight- or branched-chain alkyl, or $C_3$-$C_7$ cycloalkyl (such as cyclopentyl, cyclohexyl, hydroxymethyl and alkoxymethyl); and in Formula (C):

R, $R_1$ and $R_2$ are each independently H or $C_1$-$C_6$ straight- or branched-chain alkyl, $C_3$-$C_7$ cycloalkyl (such as cyclopentyl and cyclohexyl), $C_1$-$C_6$ straight- or branched-chain fluoroalkyls (such as fluoromethyl, difluoromethyl, trifluoromethyl and fluoroethyl), $C_2$-$C_6$ alkenyl, $C_2$-$C_6$ alkynyl, alkoxyl, t-butoxycarbonyl, t-butoxycarbonylmethyl, hydroxy, hydroxymethyl, alkoxymethyl, azido, cyano, halo, nitro, trihaloalkyl, $C_6$-$C_{10}$ aryl [such as phenyl, unsubstituted or substituted with one or more $C_1$-$C_6$ straight- or branched-chain alkyl (such as 3,4-dimethylphenyl), $C_1$-$C_6$ alkoxyl, t-butoxycarbonyl, hydroxy, azido, halo, nitro, trihaloalkyl], alkyl ($C_6$-$C_{10}$) aryl [such as a benzyl group, unsubstituted or substituted with one or more $C_1$-$C_6$ straight- or branched-chain alkyl, $C_1$-$C_6$ alkoxyl, 1,3-dioxolanyl, t-butoxycarbonyl, hydroxy, azido, halo, trihaloalkyl], and alkyldiaryls (such as diphenylmethyl), alkyldiaryl unsubstituted or substituted with one or more $C_1$-$C_6$ straight- or branched-chain alkyl, $C_1$-$C_6$ alkoxyl, 1,3-dioxolanyl or trihaloalkyl;

n=0, 1 or 2;

R' is H or $C_1$-$C_4$ straight- or branched-chain alkyl, or $C_3$-$C_7$ cycloalkyl (such as cyclopentyl, cyclohexyl); and in Formula (D):

$R_1'$, $R_2'$, $R_3'$, $R_4'$ and $R_5'$ are each independently, $C_1$-$C_6$ straight-chain alkyl (such as methyl and ethyl), or branched-chain alkyl (such as isopropyl, and isobutyl), $C_3$-$C_7$ cycloalkyls (such as cyclopentyl and cyclohexyl), $C_1$-$C_6$ straight- or branched-chain fluoroalkyls (such as fluoromethyl, difluoromethyl, trifluoromethyl, and fluoroethyl), $C_2$-$C_6$ alkenyl, $C_2$-$C_6$ alkynyl, alkoxyl, t-butoxycarbonyl, t-butoxycarbonylmethyl, halo, hydroxy, hydroxymethyl, alkoxymethyl, trihaloalkyl, $C_6$-$C_{10}$ aryl [such as phenyl, unsubstituted or substituted with one or more $C_1$-$C_6$ straight- or branched-chain alkyl (such as 3,4-dimethylphenyl), $C_1$-$C_6$ alkoxyl, t-butoxycarbonyl, halo, hydroxy, trihaloalkyl], alkyl ($C_6$-$C_{10}$) aryl (such as a benzyl group, unsubstituted or substituted with one or more $C_1$-$C_6$ straight- or branched-chain alkyl, $C_1$-$C_6$ alkoxyl, 1,3-dioxolanyl, t-butoxycarbonyl, halo, hydroxy, azido or trihaloalkyl), and alkyldiaryl (such as diphenylmethyl), unsubstituted or substituted with one or more $C_1$-$C_6$ straight- or branched-chain alkyl, $C_1$-$C_6$ alkoxyl, 1,3-dioxolanyl or trihaloalkyl;

$R_5'$ is also independently H;

$R_1'$ and $R_2'$ may be optionally tethered together to form 3- to 7-membered alicyclic ring;

$R_3'$, and $R_4'$ may be optionally tethered together to form 3- to 7-membered alicyclic ring;

n=0, 1 or 2; and

R' is H or $C_1$-$C_4$ straight- or branched-chain alkyl, or $C_3$-$C_7$ cycloalkyl (such as cyclopentyl and cyclohexyl).

The compounds of Formula (I) may exist as stereoisomers or mixtures of stereoisomers and as enantiomers or diasteroisomers, hydrates or solvates.

The novel compositions in this application are dual acting as they combine in a single molecular entity, two bioavailable, complementary, and synergistic pharmacophores, the copper sequestering property of thiomolybdates or thiotungstates, and the NMDA antagonist/antiviral activity of adamantamines (e.g. clinically useful memantine, amantadine and rimantadine) and neramexane(s). In addition, due to their compact hydrophobic structures, the compounds are inherently more stable than amm.TM under ambient conditions and possess good aqueous solubility for pharmaceutical applications. The novel thiomolybdates and thiotungstates and their pharmaceutical compositions are useful in treating and potentially arresting neurodegenerative diseases like dementia of the Alzheimer's type, other dementias such as Parkinson's, Huntington's, and AIDS-related dementia, schizophrenia and its cognitive deficits, viral infections, Wilson's disease with neurological symptoms, angiogenesis during tumor growth, liver cirrhosis, hepatitis, pulmonary fibrosis and other fibrotic diseases, cardiovascular disease, cerebral ischemia, renal anemia, rheumatoid arthritis, diabetes, obesity, gastrointestinal disorders and diseases of the eye such as glaucoma, diabetic retinopathy, and age related macular degeneration.

The compounds of Formula (I) have dual drug action. Although they have two known component parts, use of them joined as a single compound display activity greater than the two components used alone. For example, bis(1-ammonium-3,5-dimethyl-adamantane) tetrathiomolybdate was unexpectedly, 40% more effective than memantine hydrochloride at an equivalent dose (30 mg). In addition, mice receiving bis(1-ammonium-3,5-dimethyladamantane) tetrathiomolybdate (without DMSO solvate) at low, medium, and high doses were protected from tonic seizures similar to the high dose of memantine. These findings suggest a novel and more effective therapy over memantine alone. They are also effective at removal of excess unwanted free copper. The number of pills an AD patient or other patients with the above diseases would take is reduced by use of this dual action compound.

DETAILED DESCRIPTION OF THE INVENTION

Glossary

Figure 1:
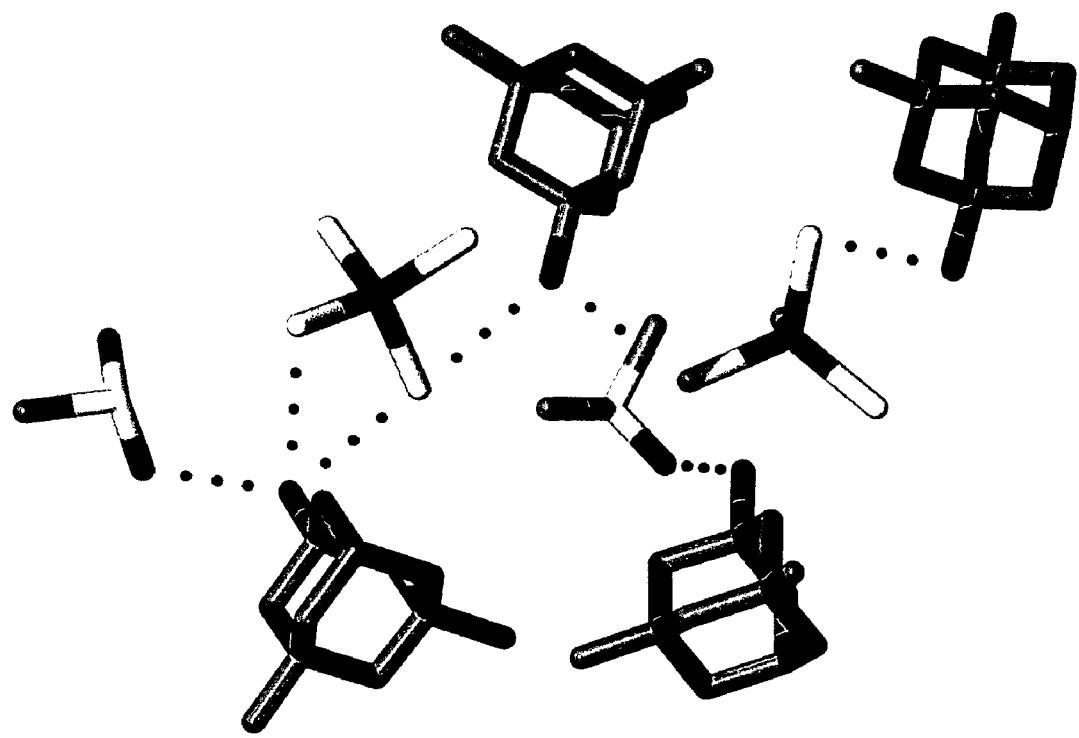
FIG. 1 illustrates the crystal structure of the product of Example 3 as a solvate with dimethylsulfoxide (DMSO), wherein the grey cyclic moieties are the 3,5-dimethyl-adamantine entities, the green with yellow atoms are the tetrathiomolybdate entities, and the red and grey moieties are molecules of dimethyl sulfoxide.
Figure 2:
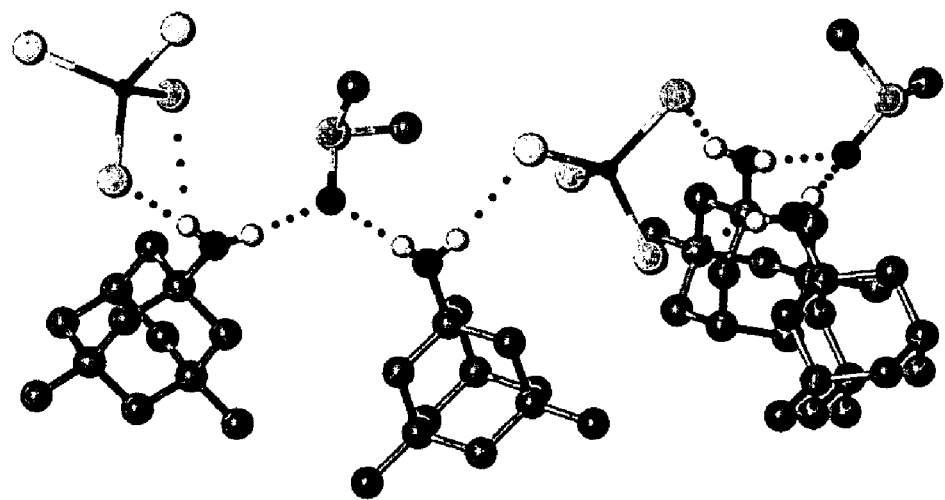
FIG. 2 illustrates the product of Example 3, without solvent, in molecular layer arrangements.
Figure 3:
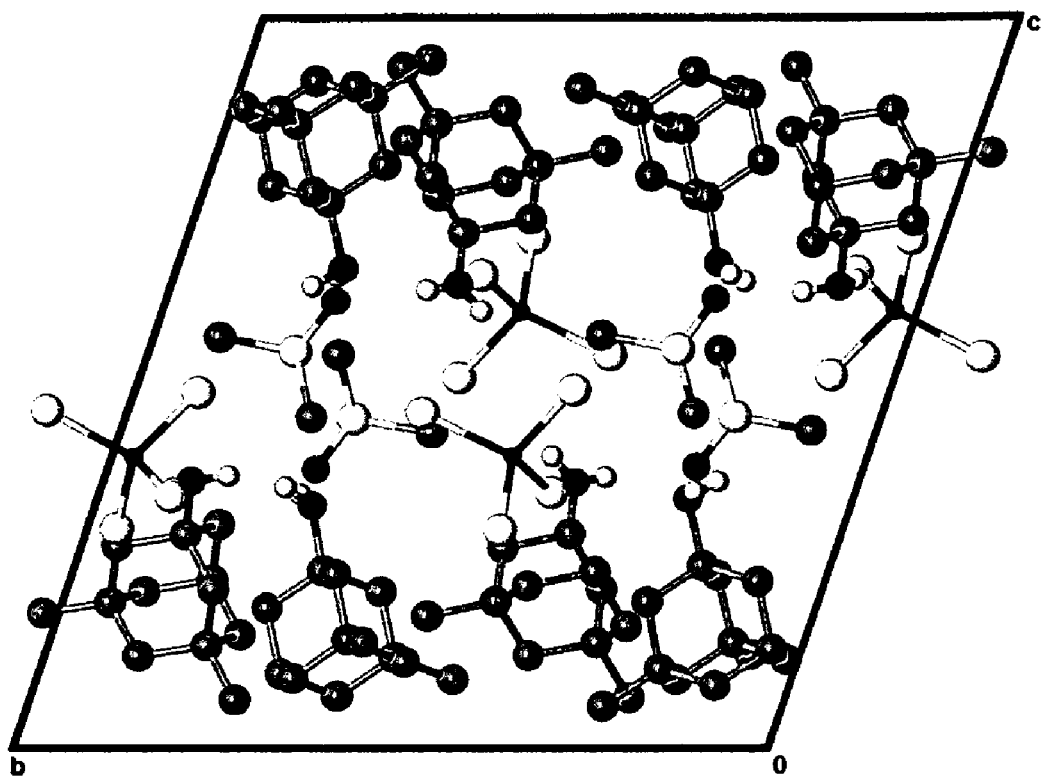
FIG. 3 illustrates the product of Example 3 in its crystal packing state with solvent DMSO.
Figure 4:
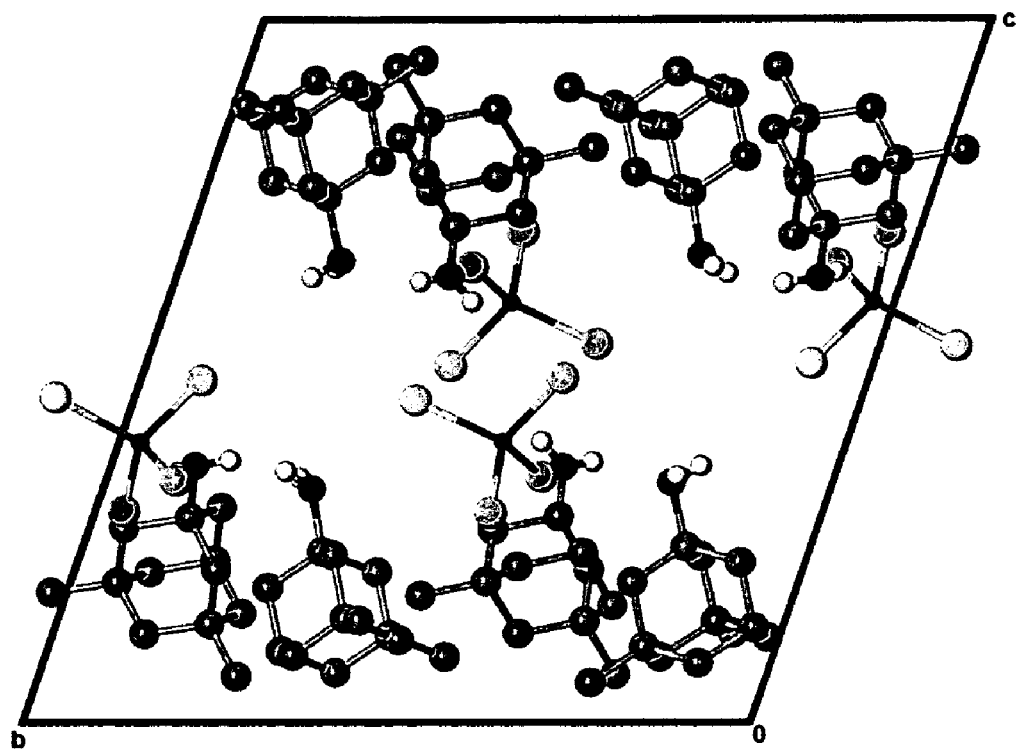
FIG. 4 illustrates the product of Example 3 in its crystalline state with all molecular attachments.

The following terms as used in this application are to be defined as stated below and for these terms, the singular includes the plural.

AChE means acetylcholinesterase

AD means Alzheimer's disease

ASTM1 means American Society for Testing and Materials standard 1 amm.TM means diammonium tetrathiomolybdate

DCM means dichloromethane

D.I.U.F. means deionized water ultrafiltered

DMSO means dimethylsulfoxide h means hour(s)

min means minute(s)

NMDA means N-methyl-D-aspartic acid

RO water means water purified through reverse osmosis.

RT means room temperature or ambient temperature, usually from 20-25° C.

The present invention provides a dual acting compound of Formula (I) incorporating two complementary, synergistic, bioavailable, pharmacophores, $$Z^+.M^{2-}.Z^+ \qquad \text{Formula (I)}$$

wherein:

$M^{2-}$ is selected from the group consisting of $MoO_3S^{2-}$, $MoO_2S_2^{2-}$, $MoOS_3^{2-}$, $MoS_4^{2-}$, $[MoS_2(S_2)_6]^{2-}$, $[Mo_2S_4(S_2)_2]^{2-}$, $[Mo_2S_4(S_4)_2]^{2-}$, $[Mo_3S(S_2)_6]^{2-}$, $WO_3S^{2-}$, $WO_2S_2^{2-}$, $WOS_3^{2-}$ and $WS_4^{2-}$;

$Z^+$ is joined to $M^{2-}$, as shown by the dot, ionically;

$Z^+$ is independently an organic ammonium moiety with an alicyclic or a polyalicyclic group of the tricyclic adamantane selected from the group as shown by Formulae (A), (B) and (C) or monoalicyclic neramexane type as shown by Formula (D), respectively, Formula (A)
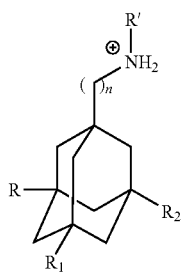

Formula (B)
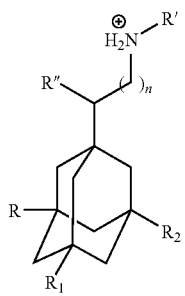

Formula (C)
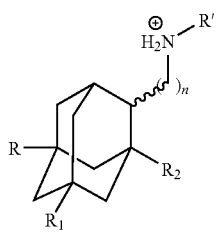

Formula (D)
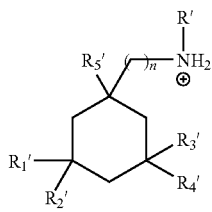

wherein:

in Formula (A):

R, $R_1$ and $R_2$ are each independently H or $C_1$-$C_6$ straight- or branched-chain alkyl, $C_3$-$C_7$ cycloalkyl (such as cyclopentyl and cyclohexyl), $C_1$-$C_6$ straight- or branched-chain fluoroalkyl (such as fluoromethyl, difluoromethyl, trifluoromethyl, fluoroethyl), $C_2$-$C_6$ alkenyl, $C_2$-$C_6$ alkynyl, alkoxyl, t-butoxycarbonyl, t-butoxycarbonylmethyl, hydroxy, hydroxymethyl, alkoxymethyl, azido, cyano, halo, nitro, trihaloalkyl, $C_1$-$C_6$ mercaptoalkyl, $C_6$-$C_{10}$ aryl [such as phenyl, unsubstituted or substituted with one or more $C_1$-$C_6$ straight- or branched-chain alkyl (such as 3,4-dimethylphenyl), $C_1$-$C_6$ alkoxyl, t-butoxycarbonyl, hydroxy, azido, halo, nitro, trihaloalkyl, or $C_1$-$C_6$ mercaptoalkyl], alkyl($C_6$-$C_{10}$ aryl) (such as a benzyl group, unsubstituted or substituted with one or more $C_1$-$C_6$ straight- or branched-chain alkyl, $C_1$-$C_6$ alkoxyl, 1,3-dioxolanyl, t-butoxycarbonyl, hydroxy, azido, halo or trihaloalkyl), and alkyldiaryl (such as diphenylmethyl, unsubstituted or substituted with one or more $C_1$-$C_6$ straight- or branched-chain alkyl, $C_1$-$C_6$ alkoxyl, 1,3-dioxolanyl, halo or trihaloalkyl);

n=0, 1 or 2; and

R' is H or $C_1$-$C_4$ straight- or branched-chain alkyl, or $C_3$-$C_7$ cycloalkyl (such as cyclopentyl and cyclohexyl).

Another aspect is compounds of Formula (I) wherein:

$M^{2-}$ is $MoS_4^{2-}$ or $WS_4^{2-}$;

$Z^+$ is an organic ammonium moiety of the tricyclic adamantane type as shown by Formula (A) wherein:

R, $R_1$ and $R_2$ are each independently H or $C_1$-$C_6$ straight- or branched-chain alkyl, $C_3$-$C_7$ cycloalkyl (such as cyclopentyl and cyclohexyl), $C_1$-$C_6$ straight- or branched-chain fluoroalkyls (such as fluoromethyl, difluoromethyl, trifluoromethyl and fluoroethyl), $C_2$-$C_6$ alkenyl, $C_2$-$C_6$ alkynyl, alkoxyl, t-butoxycarbonyl, t-butoxycarbonylmethyl, hydroxy, hydroxymethyl, alkoxymethyl, azido, cyano, halo, nitro, trihaloalkyl, $C_1$-$C_6$ mercaptoalkyl, $C_6$-$C_{10}$ aryl [such as phenyl, unsubstituted or substituted with one or more $C_1$-$C_6$ straight-chain (such as 3,4-dimethylphenyl, or branched-chain alkyl), $C_1$-$C_6$ alkoxyl, t-butoxy-carbonyl, hydroxy, azido, halo, nitro, trihaloalkyl or $C_1$-$C_6$ mercaptoalkyl], alkyl ($C_6$-$C_{10}$)aryl (such as a benzyl, unsubstituted or substituted with one or more $C_1$-$C_6$ straight- or branched-chain alkyl, $C_1$-$C_6$ alkoxyl, 1,3-dioxolanyl, t-butoxycarbonyl, hydroxy, azido, halo or trihaloalkyl), and alkyldiaryls, unsubstituted or substituted with one or more $C_1$-$C_6$ straight- or branched-chain alkyls, $C_1$-$C_6$ alkoxyl, 1,3-dioxolanyl or trihaloalkyl;

n=0, 1 or 2; and

R' is H or $C_1$-$C_4$ straight- or branched-chain alkyl, or $C_3$-$C_7$ cycloalkyl (such as cyclopentyl and cyclohexyl).

A further aspect is compounds of Formula (I) wherein:

$M^{2-}$ is $MoS_4^{2-}$ or $WS_4^{2-}$;

$Z^+$ is an organic ammonium moiety of the tricyclic adamantane type as shown by Formula (A) wherein:

R and R' are H;

$R_1$ and $R_2$ are H, methyl or ethyl; and n=0, 1 or 2.

in Formula (B):

R, $R_1$ and $R_2$ are each independently H or $C_1$-$C_6$ straight- or branched-chain alkyl, $C_3$-$C_7$ cycloalkyl (such as cyclopentyl and cyclohexyl), $C_1$-$C_6$ straight- or branched-chain fluoroalkyl (such as fluoromethyl, difluoromethyl, trifluoromethyl and fluoroethyl), $C_2$-$C_6$ alkenyl, $C_2$-$C_6$ alkynyl, alkoxyl, t-butoxycarbonyl, t-butoxycarbonylmethyl, hydroxy, hydroxymethyl, alkoxymethyl, azido, cyano, halo, nitro, trihaloalkyl, $C_1$-$C_6$ mercaptoalkyl, $C_6$-$C_{10}$ aryl [such as phenyl, unsubstituted or substituted with one or more $C_1$-$C_6$ straight- or branched-chain alkyl (such as 3,4-dimethylphenyl), $C_1$-$C_6$ alkoxyl, t-butoxycarbonyl, hydroxy, azido, halo, nitro, trihaloalkyl or $C_1$-$C_6$ mercaptoalkyl], alkyl ($C_6$-$C_{10}$) aryl [such as a benzyl group unsubstituted or substituted with one or more $C_1$-$C_6$ straight- or branched-chain alkyl, $C_1$-$C_6$ alkoxyl, 1,3-dioxolanyl, t-butoxycarbonyl, hydroxy, azido, halo or trihaloalkyl], and alkyldiaryl (such as diphenylmethyl, unsubstituted or substituted with one or more $C_1$-$C_6$ straight- or branched-chain alkyls, $C_1$-$C_6$ alkoxyl, 1,3-dioxolanyl or trihaloalkyl);

n=0, 1 or 2;

R' is H or $C_1$-$C_4$ straight- or branched-chain alkyl, or $C_3$-$C_7$ cycloalkyl (such as cyclopentyl and cyclohexyl); and R" is $C_1$-$C_4$ straight- or branched-chain alkyl, or $C_3$-$C_7$ cycloalkyl (such as cyclopentyl, cyclohexyl, hydroxymethyl and alkoxymethyl).

Another aspect is compounds of Formula (I) wherein:

$M^{2-}$ is $MoS_4^{2-}$ or $WS_4^{2-}$;

$Z^+$ is an organic ammonium moiety of the tricyclic adamantane type as shown by Formula (B) wherein:

R, $R_1$ and $R_2$ are each independently H or $C_1$-$C_6$ straight- or branched-chain alkyl, $C_3$-$C_7$ cycloalkyl (such as cyclopentyl and cyclohexyl), $C_1$-$C_6$ straight- or branched-chain fluoroalkyls (such as fluoromethyl, difluoromethyl, trifluoromethyl and fluoroethyl), $C_2$-$C_6$ alkenyl, $C_2$-$C_6$ alkynyl, alkoxyl, t-butoxycarbonyl, t-butoxycarbonylmethyl, hydroxy, hydroxymethyl, alkoxymethyl, azido, cyano, halo, nitro, trihaloalkyl, $C_1$-$C_6$ mercaptoalkyl, $C_6$-$C_{10}$ aryl [such as phenyl, unsubstituted or substituted with $C_1$-$C_6$ straight-chain (such as 3,4-dimethylphenyl, or branched-chain alkyl], $C_1$-$C_6$ alkoxyl, t-butoxycarbonyl, hydroxy, azido, halo, nitro, trihaloalkyl or $C_1$-$C_6$ mercaptoalkyl], alkyl ($C_6$-$C_{10}$)aryl (such as a benzyl, unsubstituted or substituted with $C_1$-$C_6$ straight- or branched-chain alkyl, $C_1$-$C_6$ alkoxyl, 1,3-dioxolanyl, t-butoxycarbonyl, hydroxy, azido, halo or trihaloalkyl), and alkyldiaryls, unsubstituted or substituted with $C_1$-$C_6$ straight- or branched-chain alkyls, $C_1$-$C_6$ alkoxyl, 1,3-dioxolanyl or trihaloalkyl;

n=0, 1 or 2;

R' is H or $C_1$-$C_4$ straight- or branched-chain alkyl, or $C_3$-$C_7$ cycloalkyl (such as cyclopentyl and cyclohexyl); and R" is $C_1$-$C_4$ straight- or branched-chain alkyl, or $C_3$-$C_7$ cycloalkyl (such as cyclopentyl, cyclohexyl, hydroxymethyl and alkoxymethyl).

A further aspect is compounds of Formula (I) wherein:

$M^{2-}$ is $MoS_4^{2-}$ or $WS_4^{2-}$;

$Z^+$ is an organic ammonium moiety of the tricyclic adamantine type as shown by Formula (B) wherein:

R and R' are H;

$R_1$ and $R_2$ are H, methyl or ethyl;

n=0, 1 or 2; and

R" is methyl or ethyl.

in Formula (C):

R, $R_1$ and $R_2$ are each independently H or $C_1$-$C_6$ straight- or branched-chain alkyl, $C_3$-$C_7$ cycloalkyl (such as cyclopentyl and cyclohexyl), $C_1$-$C_6$ straight- or branched-chain fluoroalkyls (such as fluoromethyl, difluoromethyl, trifluoromethyl and fluoroethyl), $C_2$-$C_6$ alkenyl, $C_2$-$C_6$ alkynyl, alkoxyl, t-butoxycarbonyl, t-butoxycarbonylmethyl, hydroxy, hydroxymethyl, alkoxymethyl, azido, cyano, halo, nitro, trihaloalkyl, $C_6$-$C_{10}$ aryl [such as phenyl, unsubstituted or substituted with one or more $C_1$-$C_6$ straight- or branched-chain alkyl (such as 3,4-dimethylphenyl), $C_1$-$C_6$ alkoxyl, t-butoxycarbonyl, hydroxy, azido, halo, nitro, trihaloalkyl], alkyl ($C_6$-$C_{10}$) aryl [such as a benzyl group, unsubstituted or substituted with one or more $C_1$-$C_6$ straight- or branched-chain alkyl, $C_1$-$C_6$ alkoxyl, 1,3-dioxolanyl, t-butoxycarbonyl, hydroxy, azido, halo, trihaloalkyl, and alkyldiaryls (such as diphenylmethyl), alkyldiaryl unsubstituted or substituted with one or more $C_1$-$C_6$ straight- or branched-chain alkyl, $C_1$-$C_6$ alkoxyl, 1,3-dioxolanyl or trihaloalkyl;

n=0, 1 or 2;

R' is H or $C_1$-$C_4$ straight- or branched-chain alkyl, or $C_3$-$C_7$ cycloalkyl (such as cyclopentyl, cyclohexyl).

Another aspect is compounds of Formula (I) wherein:

$M^{2-}$ is $MoS_4^{2-}$ or $WS_4^{2-}$;

$Z^+$ is an organic ammonium moiety of the tricyclic adamantane type as shown by Formula (C) wherein:

R, $R_1$ and $R_2$ are each independently H or $C_1$-$C_6$ straight- or branched-chain alkyl, $C_3$-$C_7$ cycloalkyl (such as cyclopentyl and cyclohexyl), $C_1$-$C_6$ straight- or branched-chain fluoroalkyls (such as fluoromethyl, difluoromethyl, trifluoromethyl and fluoroethyl), $C_2$-$C_6$ alkenyl, $C_2$-$C_6$ alkynyl, alkoxyl, t-butoxycarbonyl, t-butoxycarbonylmethyl, hydroxy, hydroxymethyl, alkoxymethyl, azido, cyano, halo, nitro, trihaloalkyl, $C_1$-$C_6$ mercaptoalkyl, $C_6$-$C_{10}$ aryl [such as phenyl, unsubstituted or substituted with $C_1$-$C_6$ straight-chain (such as 3,4-dimethylphenyl, or branched-chain alkyl), $C_1$-$C_6$ alkoxyl, t-butoxycarbonyl, hydroxy, azido, halo, nitro, trihaloalkyl or $C_1$-$C_6$ mercaptoalkyl], alkyl ($C_6$-$C_{10}$)aryl [such as a benzyl group, unsubstituted or substituted with $C_1$-$C_6$ straight- or branched-chain alkyl, $C_1$-$C_6$ alkoxyl, 1,3-dioxolanyl, t-butoxycarbonyl, hydroxy, azido, halo or trihaloalkyl], and alkyldiaryls, unsubstituted or substituted with $C_1$-$C_6$ straight- or branched-chain alkyls, $C_1$-$C_6$ alkoxyl, 1,3-dioxolanyl or trihaloalkyl;

n=0, 1 or 2; and

R' is H or $C_1$-$C_4$ straight- or branched-chain alkyl, or $C_3$-$C_7$ cycloalkyl (such as cyclopentyl, and cyclohexyl).

A further aspect is compounds of Formula (I) wherein:

$M^{2-}$ is $MoS_4^{2-}$ or $WS_4^{2-}$;

$Z^+$ is an organic ammonium moiety of the tricyclic adamantane type as shown by Formula (C) wherein:

R and R' are H;

$R_1$ and $R_2$ are H, methyl or ethyl;

n=0, 1 or 2.

in Formula (D):

$R_1'$, $R_2'$, $R_3'$, $R_4'$ and $R_5'$ are each independently, $C_1$-$C_6$ straight-chain alkyl (such as methyl and ethyl), or branched-chain alkyl (such as isopropyl, and isobutyl), $C_3$-$C_7$ cycloalkyls (such as cyclopentyl and cyclohexyl), $C_1$-$C_6$ straight- or branched-chain fluoroalkyls (such as fluoromethyl, difluoromethyl, trifluoromethyl, and fluoroethyl), $C_2$-$C_6$ alkenyl, $C_2$-$C_6$ alkynyl, alkoxyl, t-butoxycarbonyl, t-butoxycarbonylmethyl, halo, hydroxy, hydroxymethyl, alkoxymethyl, trihaloalkyl, $C_6$-$C_{10}$ aryl [such as phenyl, unsubstituted or substituted with one or more $C_1$-$C_6$ straight- or branched-chain alkyl (such as 3,4-dimethylphenyl), $C_1$-$C_6$ alkoxyl, t-butoxycarbonyl, halo, hydroxy, trihaloalkyl], alkyl ($C_6$-$C_{10}$) aryl (such as a benzyl group, unsubstituted or substituted with one or more $C_1$-$C_6$ straight- or branched-chain alkyl, $C_1$-$C_6$ alkoxyl, 1,3-dioxolanyl, t-butoxycarbonyl, halo, hydroxy, azido or trihaloalkyl), and alkyldiaryl (such as diphenylmethyl), unsubstituted or substituted with one or more $C_1$-$C_6$ straight- or branched-chain alkyl, $C_1$-$C_6$ alkoxyl, 1,3-dioxolanyl or trihaloalkyl;

$R_5'$ is also independently H;

$R_1'$ and $R_2'$ may be optionally tethered together to form 3- to 7-membered alicyclic ring;

$R_3'$ and $R_4'$ may be optionally tethered together to form 3- to 7-membered alicyclic ring;

n=0, 1 or 2; and

R' is H or $C_1$-$C_4$ straight- or branched-chain alkyl, or $C_3$-$C_7$ cycloalkyl (such as cyclopentyl and cyclohexyl).

Another aspect is compounds of Formula (I) wherein:

$M^{2-}$ is $MoS_4^{2-}$ or $WS_4^{2-}$;

$Z^+$ is an organic ammonium moiety of the monoalicyclic neramexane type as shown by Formula (D) wherein:

$R_1'$, $R_2'$, $R_3'$, $R_4'$ and $R_5'$ are each independently, $C_1$-$C_6$ straight-chain such as methyl, ethyl, or branched-chain alkyl, $C_3$-$C_7$ cycloalkyl (such as cyclopentyl and cyclohexyl), $C_1$-$C_6$ straight- or branched-chain fluoroalkyl (such as fluoromethyl, difluoromethyl, trifluoromethyl and fluoroethyl), $C_2$-$C_6$ alkenyl, $C_2$-$C_6$ alkynyl, alkoxyl, t-butoxycarbonyl, t-butoxycarbonylmethyl, halo, hydroxy, hydroxymethyl, alkoxymethyl, trihaloalkyl, $C_6$-$C_{10}$ aryl [such as phenyl, unsubstituted or substituted with one or more $C_1$-$C_6$ straight-chain (such as 3,4-dimethylphenyl) or branched-chain alkyl, $C_1$-$C_6$ alkoxyl, t-butoxy-carbonyl, halo, hydroxy or trihaloalkyl], alkyl ($C_6$-$C_{10}$) aryl (such as a benzyl group, unsubstituted or substituted with $C_1$-$C_6$ straight- or branched-chain alkyl, $C_1$-$C_6$ alkoxyl, 1,3-dioxolanyl, t-butoxycarbonyl, halo, hydroxy, azido or trihaloalkyl), and alkyldiaryls (such as diphenylmethyl, unsubstituted or substituted with $C_1$-$C_6$ straight- or branched-chain alkyls, $C_1$-$C_6$ alkoxyl, 1,3-dioxolanyl or trihaloalkyl);

$R_5'$ is also independently H;

$R_1'$ and $R_2'$ may be optionally tethered together to form 3- to 7-membered alicyclic ring;

$R_3'$ and $R_4'$ may be optionally tethered together to form 3- to 7-membered alicyclic ring;

n=0, 1 or 2; and

R' is H or $C_1$-$C_4$ straight- or branched-chain alkyl, or $C_3$-$C_7$ cycloalkyl (such as cyclopentyl, and cyclohexyl).

A further aspect is compounds of Formula (I) wherein:

$M^{2-}$ is $MoS_4^{2-}$ or $WS_4^{2-}$;

$Z^+$ is an organic ammonium moiety of the monoalicyclic neramexane type as shown by Formula (D) wherein:

$R_1'$, $R_2'$, $R_3'$, and $R_4'$ are each independently methyl or ethyl;

$R_5'$ is H, methyl or ethyl;

n=0, 1 or 2; and

R' is H.

In another aspect of this invention, the use of tetrathiomolybdate or tetrathiotungstate salts of known compounds for the treatment of AD diseases, such as dimebon (generic name for CAS 3613-73-8; 3,6-dimethyl-9-(2-methylpyridyl-5) ethyl-1,2,3,4-tetrahydro-γ-carboline), are expected to produce similar results of the advantages with these salts.

The compounds of Formula (I) may exist as stereoisomers or mixtures of stereoisomers and as enantiomers or diasteroisomers, hydrates, or as solvates.

Pharmacology:

Compounds of Examples 1-4 were tested in vivo, for their N-methyl-D-aspartate (NMDA) antagonist properties. Briefly, the test measures blockage of seizure activity and lethality in mice produced by the administration of NMDA when pretreated with the antagonists. [see Leander, J. D., et al., *Brain Res.* 448, 115-120 (1988) and Parsons, C. G., et al., *Neuropharmacol* 34, 1239-1258; (1995)]. These studies demonstrated that pretreatment with memantine thiomolybdate (SSV-0032; bis(1-ammonium-3,5-dimethyladamantane) tetrathiomolybdate) inhibited NMDA-induced clonic seizures and mortality in a dose dependent manner. Moreover, by this measure, bis(1-ammonium-3,5-dimethyladamantane) tetrathiomolybdate was unexpectedly, 40% more effective than memantine at an equivalent dose (30 mg). In addition, mice receiving bis(1-ammonium-3,5-dimethyladamantane) tetrathiomolybdate (without the DMSO solvate) at low, medium, and high doses were protected from tonic seizures similar to the high dose of memantine. These findings suggest a novel and more effective therapy over memantine alone.

Test protocol: Groups of 5 male CD-1 mice weighing 24±2 g were used. Male CD-1 (Crl.) mice were provided by Bio-Lasco Taiwan (under Charles River Laboratories Technology License). Space allocations for animals were as follows: 29×18×13 cm for 5 mice. Mice were maintained in a controlled temperature (22° C.-24° C.) and humidity (60%-80%) environment with 12 h light/dark cycles for at least one week in MDS Pharma Services—Taiwan Laboratory prior to use. Free access to standard lab chow for mice [MF-18 (Oriental Yeast Co., Ltd., Japan)] and RO water was granted. [All aspects of this work including housing, experimentation and disposal of animals were performed in general accordance with the Guide for the Care and Use of Laboratory Animals (National Academy Press, Washington, D.C., 1996).]

Test substance was administered by subcutaneous (sc) injection 20 min before challenge with NMDA 200 mg/kg by intraperitoneal injection (IP). The animals were placed individually in glass jars and observed over a period of 4 h for presence of clonic convulsions, tonic convulsions and mortality. The onset of clonic and tonic convulsions as well as death was recorded and incidence of clonic seizures, tonic seizures and death was reported. Inhibition of NMDA (200 mg/kg, IP)-induced tonic convulsions/mortality (mainly mortality) in more than 50 percent (>50%) of the 5 mice during the following 4 h indicates possible NMDA receptor antagonist activity. Memantine hydrochloride at 30 mg/kg sc was used as positive control.

Figure 5:
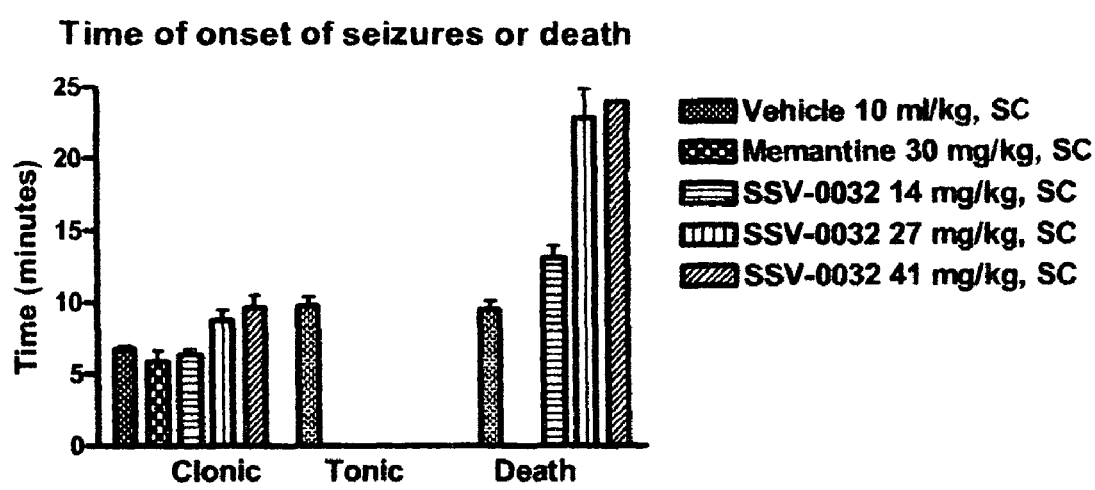
FIG. 5 shows the results for the time of onset of NMDA induced seizures after pretreatment with bis(1-ammonium-3,5-dimethyladamantane) tetrathiomolybdate [SSV-0032 in the Fig,] at three doses with memantine hydrochloride as positive control.
Figure 6:
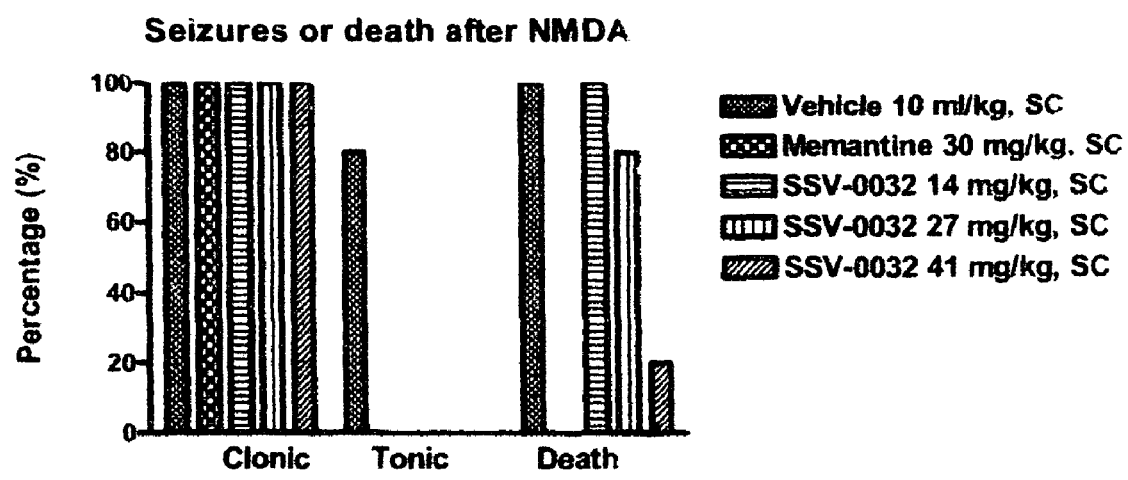
FIG. 6 shows the results for survival following NMDA induced seizures after pretreatment with bis(1-ammonium-3,5-dimethyladamantane) tetrathiomolybdate [SSV-0032 in the Fig,] at three doses with memantine hydrochloride as positive control.

The vehicle used for dissolution was 20% aqueous DMSO. Thus, as shown in FIGS. 5 and 6, compound of Example 3, bis(1-ammonium-3,5-dimethyladamantane) tetrathiomolybdate blocked the effects of NMDA induced seizures in a dose dependent manner. At the highest equivalent memantine dose, 4/5 mice survived vs 5/5 for memantine. However, the time to seizures was notably prolonged. The bis(neramexane) tetrathiomolybdate, compound of Example 4, demonstrated complete protection at equivalent memantine dose. The compounds of Examples 1 and 2 were administered as suspensions due to inadequate solubility in the vehicle, and thus were not protective in the test.

Formulations

The present invention provides compositions, pharmaceutically acceptable formulations and kits, which on administering release not only therapeutically useful thiomolybdic or thiotungstic acids, but also pharmacologically active organic alkylammonium species of this invention. The novel thiomolybdates of Formula (I) and their pharmaceutical compositions are useful in preventing and treating neurodegenerative diseases like Alzheimer's (AD), dementias of Alzheimer's, Parkinson's and AIDS, schizophrenia and its cognitive deficits, viral infections, Wilson's disease with neurological symptoms, angiogenesis during tumor growth, liver cirrhosis, hepatitis, pulmonary fibrosis and other fibrotic diseases, cardiovascular disease, cerebral ischemia, renal anemia, rheumatoid arthritis, diabetes, obesity, gastrointestinal disorders and diseases of the eye such as glaucoma, diabetic retinopathy, and age related macular degeneration.

In cases of initial high copper toxicities, the patients may be acutely treated with other potent copper-lowering drugs such as trientine or penicillamine, and later switched to lifelong therapy with agents of the present invention.

Additionally the present formulation may be used in combination with an AChE inhibitor, such as donepezil, rivastigmine, tacrine or galanthamine.

Mixtures of the various compounds of Formula (I) may also be used, but not Mo compounds mixed with W compounds.

The pharmaceutical composition may also contain physiologically tolerable diluents, carriers, adjuvants, and the like. The phrase "pharmaceutically-acceptable" means those formulations which are, within the scope of sound medical judgment, suitable for use in contact with the tissues of humans and animals without undue toxicity, irritation, allergic response and the like, and are commensurate with a reasonable benefit/risk ratio. The pharmaceutical compositions of Formula (I) can be administered to humans and other mammals enterally or parenterally in a solid, liquid, or vapor form. Parenteral routes include intravenous, intramuscular, intraperitoneal, infrasternal, and subcutaneous injection or infusion. These compositions can also be delivered through a catheter for local delivery at a target site, via an intracoronary stent (a tubular device composed of a fine wire mesh), or via a biodegradable polymer. The active compound(s) is mixed under sterile conditions with a pharmaceutically acceptable carrier along with any needed preservatives, excipients, buffers or propellants. Ophthalmic formulations, eye ointments, powders and solutions are also contemplated as being within the scope of this invention.

Actual dosage levels of the active ingredients of Formula (I) in the pharmaceutical formulation can be varied so as to achieve the desired therapeutic response for a particular patient. The selected dosage level will depend upon the activity of the particular compound, the route of administration, the severity of the condition being treated, and prior medical history of the patient being treated. This evaluation of dose is well within the ability of the medical staff as one skilled in this art to determine.

The phrase "therapeutically effective amount" of the compound of Formula (I) means a sufficient amount of the compound to treat disorders, at a reasonable benefit/risk ratio applicable to medical treatment. It will be understood, however, that the total daily usage of the compounds and compositions of the present invention shown by Formula (I) will be decided based on clinical experience. The specific therapeutically effective dose level for any particular patient will depend upon a variety of factors, including but not limited to: the disorder being treated; the severity of the disorder; activity of the specific compound employed; the number of doses administered in a specified time; the specific composition employed; age, body weight, general health, sex, and diet of the patient; the time of administration; route of administration; rate of excretion of the specific compound employed; and the duration of the treatment. The compounds of Formula (I) may also be administered in combination with other drugs, if medically deemed necessary, to treat the disorder concerned.

An aspect of the present compounds' composition as a salt form is their inherent chemical stability, when compared with an admixture of the single components. The two-combination admixture is not otherwise chemically compatible so is unsuitable to use. To demonstrate the unique compound structure, results of a single crystal X-ray structure of bis(1-ammonium-3,5-dimethyladamantane) tetrathiomolybdate confirmed its 2:1 memantine:tetrathiomolybdic acid formula. Additionally, the present compositions provide ease of formulation, manufacture and stability, as well as ease of use in terms of clinical trial design and patient compliance as the patient has fewer pills to take.

Compositions suitable for parenteral injection may comprise physiologically acceptable, sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include: water, ethanol, polyols (propylene glycol, polyethyleneglycol, glycerol, and the like), vegetable oils (such as olive oil), injectable organic esters such as ethyl oleate, and suitable mixtures thereof. These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like.

Suspensions, in addition to the compounds of Formula (I), may contain suspending agents, as for example, ethoxylated isostearyl alcohols, polyoxyethylene sorbitan esters, microcrystalline cellulose, aluminum metahydroxide, bentonite, agar-agar and tragacanth, or mixtures of these substances, and the like. Prolonged absorption of the injectable pharmaceutical form can be brought about by the use of agents delaying absorption, for example, aluminum monostearate and gelatin. Proper fluidity can be maintained, for example, by the use of coating materials such as lecithin, by the maintenance of the required particle size in the case of dispersions, and by the use of surfactants. In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending on the ratio of drug to polymer and the nature of the particular polymer employed, the rate of the drug release can be controlled. Examples of other biodegradable polymers include poly(orthoesters) and poly(anhydrides). Depot injectable formulations are also prepared by entrapping the drug in liposomes or microemulsions, which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Dosage forms for topical administration of the compounds of Formula (I) include powders, sprays, eye drops, ointments, patch and inhalants.

Solid dosage forms for oral administration include capsules, tablets, pills, powders and granules. In such solid dosage forms, the active compound may be mixed with at least one inert, pharmaceutically-acceptable excipient or carrier, such as sodium citrate or dicalcium phosphate and/or a) fillers or extenders such as starches, lactose, sucrose, glucose, mannitol, and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof.

Solid compositions of a similar type may also be employed as fillers in soft and hard-filled gelatin capsules using such excipients as lactose or milk sugar as well as high molecular weight polyethylene glycols and the like. The solid dosage forms of tablets, capsules, pills and granules can be prepared with coatings and shells such as enteric coatings and other coatings well known in the pharmaceutical formulating art. They may optionally contain opacifying agents and may also be of a composition such that they release the active ingredient(s) only, or preferentially, in a certain part of the intestinal tract, optionally in a delayed manner. Examples of embedding compositions, which can be used, include polymeric substances and waxes. The active compounds can also be in microencapsulated form, if appropriate, with one of more of the above-mentioned excipients.

Compositions of the compounds of Formula (I) for rectal or vaginal administration are preferably suppositories which can be prepared by mixing the compounds of Formula (I) with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of Formula (I) can also be administered in the form of liposomes. As is known in the art, liposomes are generally derived from phospholipids or other lipid substances. Liposomes are formed by mono- or multi-lamellar hydrated liquid crystals, which are dispersed in an aqueous medium. Any non-toxic, physiologically acceptable and metabolizable lipid capable of forming liposomes can be used. The present invention compositions in liposome form can contain, in addition to a compound of Formula (I), stabilizers, preservatives, excipients and the like. The preferred lipids are natural and synthetic phospholipids and phosphatidyl cholines (lecithins) used separately or together. Methods to form liposomes are well known in the art [e.g., *Liposomes in Biomedical Applications; Drug Targeting and Delivery*, Vol. 6, by P. N. Shek, pub. CRC (Aug. 3, 1995)].

Liquid dosage forms for oral administration include pharmaceutically acceptable emulsions, solutions, suspensions, syrups and elixirs. In addition to the compounds of Formula (I), the liquid dosage forms may contain inert diluents commonly used in the art such as, for example, water or other solvents, solubilizing agents and emulsifiers such as ethyl alcohol, isopropyl alcohol, ethyl carbonate, stablizers, excipients, buffers when needed, preservatives and other common additives.

Another aspect of the compounds of the present invention is the fixed, relatively low dose of the thiomolybdic acid. For example, based on the clinically recommended maximum daily dose of 20 mg memantine hydrochloride (divided into 10 mg twice daily), bis(1-ammonium-3,5-dimethyladamantane) tetrathiomolybdate, can be dosed up to 14 mg twice daily. This dose will deliver the effective dose of memantine in a current 10 mg pill, and tetrathiomolybdic acid at 5.3 mg twice daily. When given with food, this level of dosing is sufficient to remove 2-4 mg of copper per day from food sources and endogenous secretions (e.g., saliva, gastric juice, and other sources). The low dose of tetrathiomolybdic acid will allow for its long-term use for copper levels attenuation therapy in AD and other mentioned diseases, without adversely affecting essential copper-dependent physiological processes such as heme synthesis and cell proliferation. In cases of initial high copper toxicities, the patients may be acutely treated with other potent copper-lowering drugs such as trientine or penicillamine, and later switched to life long therapy with compounds of the present invention. This treatment variation is within the scope of the present invention.

Equipment and Methods

General methods of preparation of compounds of Formula I are described below. The products were characterized by melting point, elemental analysis, $^1$H and $^{13}$C NMR, and UV, and single crystal x-ray crystallography. The starting materials were purchased from Aldrich Chemical Co., Acros, Mallinckrodt or Fisher Scientific Co. Neramexane was synthesized in three steps by the method of Jirgensons, A., et al., *Synthesis* 12, 1709-1719 (2000).

Method A: is based on the procedure of B. Srinivasan et al., Zeitschrift fuer Naturforschung, B: *Chemical Sciences* 59(10), 1083-1092 (2004). It involves base promoted cation exchange in the reaction of diammonium salt of tetrathiomolybdic acid or diammonium salt of tetrathiotungstic acid with an organic amine or organic ammonium hydroxide, and distilling off the volatile ammonia. The precipitated product is purified by recrystallization from aqueous or aqueous-alcohol media.

Alternatively, to an aqueous solution of the organic amine hydrochloride, is slowly added an aqueous solution containing stoichiometric amount of ammonium tetrathiomolybdate or ammonium tetrathiotungstate. After stirring for 4-6 hours, the suspension is cooled to 5-10° C. and the product filtered. The solid product is washed with cold water until the filtrate contains no chloride ions. Then the product is washed with alcohol and dried in vacuo at 60-80° C. under a stream of nitrogen.

Method B: is based on the classical method to prepare ammonium tetrathiomolybdate. Molybdenum tetraoxide ($MoO_4$) is suspended in an excess of an aqueous solution of the organic amine, and then hydrogen sulfide gas is passed into the well-stirred solution/suspension at ambient temperature when complete solution occurs. After reaction over 18-24 hours the precipitated product is collected, washed well with cold distilled water, anhydrous ethanol, and dried in vacuo at 60-80° C. under a stream of nitrogen gas.

Method C: is an alternative to Method B. A stoichiometric solution of an organic amine sulfide in water is first prepared by reaction of the amine with hydrogen sulfide. To an excess of this solution is added $MoO_4$ and the mixture stirred over 18-24 hours. The product is isolated as in Method B.

Method D: is based on the method of Liu, C et al., Chinese Patent application CN 2004-10039454. The diammonium paramolybdate [$(NH_4)_6Mo_7O_{24}.4H_2O$] or molybdenum trioxide ($MoO_3$) is treated with a stoichiometric amount of organic amine sulfide solution in water. The reaction occurs under mild conditions in 4-24 hours. The product is collected, washed with cold water, absolute ethanol, and dried in vacuo at 60-80° C. under a stream of nitrogen gas.

Alternatively, ammonium tetrathiomolybdate is generated in situ from $MoO_3$, ammonium hydroxide and ammonium sulfide, and then a solution of the organic amine added. The product is isolated as in Method A.

The invention will be further clarified by a consideration of the following examples, which are intended to be purely exemplary of the present invention.

Example 1

Bis(1-ammoniumadamantane) tetrathiomolybdate [Formula (I) A]

Aminoadamantane (0.90 g, 5.95 mmol, Aldrich) was dissolved in 2-propanol (75 mL) and added to bis(ammonium) tetrathiomolybdate (780 mg, 2.99 mmol) in water (ASTM1, 100 mL) at RT. After mixing for 30 mins., the 2-propanol was removed on a rotary evaporator at RT. The remaining aqueous mixture was stored for 2 h in a refrigerator. The dark orange solid was filtered and washed with cold water (15 mL) and diethyl ether (15 mL). The solid was dried to a constant weight at RT. The product obtained was bis(1-ammoniumadamantane) tetrathiomolybdate (1.50 g, 95% yield) as an orange solid (melting point; 220° C. dec.). Its spectra are as follows:

$^1$H NMR (300 MHz, DMSO-d$_6$): δ 7.72 (br s, 6H), 2.06 (s, 6H), 1.78 (s, 12H), 1.63 (m 12H);

$^{13}$C NMR (75 MHz, DMSO-d$_6$): δ 51.03, 39.80, 35.07, 28.35;

UV-Vis (ethanol): 318, 243, 193; and
CHN analysis: Calculated for: $C_{20}H_{36}MoN_2S_4$.
Calculated: C, 45.43; H, 6.86; N, 5.30; S: 24.26.
Found: C, 45.39; H, 6.97; N, 5.26; S: 24.39.

Example 2

Bis(1-methylammoniumadamantane) tetrathiomolybdate [Formula (I), B]

1-Methylaminoadamantane (0.99 g, 5.98 mmol, Aldrich) was dissolved in 2-propanol (75 mL) and added to bis(ammonium) tetrathiomolybdate (780 mg, 2.99 mmol) in water (ASTM1, 100 mL) at RT. After mixing for 30 mins, the 2-propanol was removed on a rotary evaporator at RT. The remaining aqueous mixture was stored for 2 h in a refrigerator. The dark orange solid was filtered and washed with cold water (15 mL) and diethyl ether (15 mL). The solid was dried to a constant weight at RT. The product was bis(1-methylammoniumadamantane) tetrathiomolybdate (1.60 g, 97% yield) as an orange solid (melting point; 168° C. dec.). Its spectra are as follows:

$^1$H NMR (300 MHz, DMSO-$d_6$): δ 7.49 (br s, 6H), 2.52 (s, 4H), 1.94 (s, 6H), 1.60 (m, 12H), 1.50 (s, 12H);

$^{13}$C NMR (75 MHz, DMSO-$d_6$): δ 50.42, 8.75, 36.08, 31.60, 27.37;

UV-Vis (ethanol): 318, 243, 193; and
CHN analysis: Calculated for: $C_{22}H_{40}MoN_2S_4$.
Calculated: C, 47.46; H, 7.24; N, 5.03; S: 23.04.
Found: C, 47.41; H, 7.47; N, 5.05; S: 23.05.

Example 3

Bis(1-ammonium-3,5-dimethyladamantane) tetrathiomolybdate [Formula (I), A]

The free base of memantine was prepared from the hydrochloride salt (Acros) by dissolving the salt (1.0 g) in water (25 mL). Sodium hydroxide (2 g) in water (10 mL) was added and the free amine was extracted with DCM (2×25 mL). The combined DCM fractions were dried over anhydrous sodium sulfate, filtered, and concentrated. The remaining clear oil (0.8 g, 4.46 mmol) was dissolved in 2-propanol (30 mL) and added to bis(ammonium) tetrathiomolybdate (580 mg, 2.23 mmol) in warm water (30 mL). After mixing for 30 mins, the 2-propanol was removed on a rotary evaporator at RT. The remaining aqueous mixture was stored for 2 h in a refrigerator. The dark orange solid was filtered and washed with cold water (15 mL) and diethyl ether (15 mL). The solid was dried to a constant weight at RT. This provided as a product bis(1-ammonium-3,5-dimethyladamantane) tetrathiomolybdate (1.15 g, 88% yield) as a dark orange solid (melting point; 135° C. dec.). Its spectra are as follows:

$^1$H NMR (300 MHz, DMSO-$d_6$): δ 5.0 (br s, 6H), 2.50 (br s, 2H), 2.14 (br s, 2H), 1.61 (s, 4H), 1.43 (d, 4H, J=12 Hz), 1.36 (d, 4H, J=12 Hz), 1.28 (s, 6H), 1.14 (d, 2H, J=13 Hz), 1.07 (d, 2H, J=13 Hz), 0.84 (s, 12H);

$^{13}$C NMR (75 MHz, DMSO-$d_6$): δ 52.17, 49.44, 46.23, 41.45, 38.82, 32.00, 29.63, 29.16;

UV-Vis (water): 318, 243, 195; and
CHN analysis: Best fit calculated for: $C_{24}H_{44}MoN_2S_4 \cdot 0.4H_2O$
Calculated: C, 49.29; H, 7.58; N, 4.79; S: 21.93.
Found: C, 48.55; H, 7.47; N, 4.71; S: 21.70.
Best fit: C, 48.69; H, 7.63; N, 4.73; S: 21.66.
(sample retained 1.2% water after drying).

A single crystal for x-ray diffraction studies was carefully produced in the following manner.

A test tube (5 mL) was charged with powder obtained above (10.0 mg) and dissolved in a minimum amount of DMSO (0.05 mL). A microliter syringe was used to insert a small drop of degassed water. A powder immediately formed. The solid was dissolved with more DMSO (0.10 mL) and a drop of water was dripped into the test tube. A powder formed immediately but dissolved again after swirling. The test tube was allowed to stand at RT over several days. Small ruby red crystals were obtained. One crystal was submitted for x-ray diffraction study.

Crystallography. X-ray data were collected on a Siemens P4 diffractometer using a graphite monochromatic Cu Kα radiation (λ=1.54178 Å) and XSCANS (Bruker, version 2.31) software package. The data set was collected at 25° C. and corrected for Lorentz and polarization effects. Data were corrected for absorption (XPREP, version 2006/1). Crystal stability was monitored by measuring three standard reflections every 97 reflections with no significant variations (<±3%). The X-SEED software platform, equipped with SHELX modules on a PC computer, was used for all structure solution (SHELXS-97) and refinement (SHELXL-97) calculations and molecular graphics. The structure was solved by direct methods, and refined by anisotropic full-matrix least-squares for all non-hydrogen atoms.

The function, $\Sigma w(|Fo|^2-|Fc|^2)^2$, was minimized, where $w=q/[\sigma^2(F_O^2)+(aP)^2+bP+d+e \sin\theta]$ and $P=f[\max(f$ or $F_O^2)]+(1-F)F_C^2$.

All non-hydrogen atoms were refined with anisotropic displacement parameters. All hydrogen atoms were assigned ideal positions and refined using a riding model. See Table 1 below.

TABLE 1

Crystal data and structure refinement for Bis(1-ammonium-3,5-dimethyladamantane) tetrathiomolybdate

| | |
|---|---|
| Empirical formula | $C_{52}H_{96}Mo_2N_4O_2S_{10}$ |
| Formula weight | 1321.81 g mol$^{-1}$ |
| Temperature | 298(2) K |
| Wavelength | 0.71073 Å |
| Crystal system | Triclinic |
| Space group | P-1 |
| Unit cell dimensions | a = 12.4992(18) Å  α = 108.395(8)° |
| | b = 16.394(2) Å  β = 97.331(10)° |
| | c = 17.2352(19) Å  γ = 90.995(10)° |
| Volume | 3317.6(7) Å$^3$ |
| Z | 2 |
| Density (calculated) | 1.323 |
| Absorption coefficient | 0.731 mm$^{-1}$ |
| F(000) | 1392 |
| Theta range for data collection | 2.04 to 25.35° |
| Reflections collected | 13930 |
| Independent reflections | 5985 [R(int) = 0.0594] |
| Max. and min. transmission | 0.7789 and 0.9575 |
| Goodness-of-fit on F$^2$ | 0.989 |
| Final R indices [I > 2sigma(I)] | R1 = 0.0701, wR2 = 0.1132 |
| R indices (all data) | R1 = 0.1704, wR2 = 0.1451 |

Example 4

Bis(1-ammonium-1,3,3,5,5-pentamethylcyclohexane)tetrathiomolybdate [Formula (I), D]

Neramexane (1.0 g, 5.9 mmol) was dissolved in 2-propanol (75 mL) and added to bis(ammonium) tetrathiomolybdate (780 mg, 2.99 mmol) in water (ASTM1, 100 mL) at RT. After mixing for 30 mins, the 2-propanol was removed on a rotary evaporator at RT. The remaining aqueous mixture was stored for 2 h in a refrigerator. The dark orange solid was filtered and washed with cold water (15 mL) and diethyl ether (15 mL). The solid was dried to a constant weight at RT. This provided as the product bis(1-ammonium-1,3,3,5,5-pentamethylcyclohexane) tetrathiomolybdate (1.50 g, 95% yield) as a dark orange solid (melting point; 20° C. dec.). Its spectra are as follows:

$^1$H NMR (300 MHz, DMSO-$d_6$): δ 7.53 (br s, 6H), 1.56 (d, 4H, J=13.4 Hz), 1.42-1.39 (m, 10H), 1.28 (d, 2H, J=13.8 Hz), 1.08-1.00 (m, 14H), 0.92 (br s, 12H);

$^{13}$C NMR (75 MHz, DMSO-$d_6$): δ 50.60, 49.79, 46.53, 35.49, 31.10, 28.92, 26.44;

UV-Vis (ethanol): 317, 243, 197; and

CHN analysis: Best fit calculated for: $C_{22}H_{48}MoN_2S_4 \cdot 0.9H_2O$

Calculated: C, 46.78; H, 8.57; N, 4.96; S: 22.71.
Found: C, 45.38; H, 8.59; N, 4.85; S: 22.06.
Best fit: C, 45.48; H, 8.64; N, 4.82; S: 22.07.

(2.7% water retained after drying at RT. Drying at higher temperatures led to decomposition.)

Example 5

(±)Bis(1-ammonium-1-(1-adamantyl)ethane] tetrathiomolybdate [Formula (I), B]

A solution of ammonium tetrathiomolybdate (0.26 g, 0.98 mmol) in D.I.U.F. water (5.0 mL) was added dropwise at RT to a stirred solution of 1-(1-adamantyl)ethylamine hydrochloride (0.43 g, 2.0 mmol) in D.I.U.F. water (8.0 mL). An orange solid formed. The suspension was stirred at RT for 0.5 h and under ice cooling (5° C., bath) for 1 h. The formed solids were filtered off, washed twice with ice-cold D.I.U.F. water (1.0 mL each time) and dried in vacuum (1 mmHg) at 50° C. for 19.5 h to yield 0.55 g (95.9%) of title compound as an orange solid, m.p. 138-140° C. Its spectra are as follows:

$^1$H NMR (300 MHz, DMSO-$d_6$): δ 7.51 (br, 6H), 3.81 (q, J=6.5 Hz, 2H), 1.97 (br s, 6H), 1.69-1.46 (m, 24H), 1.09 (d, J=6.5 Hz, 6H);

$^{13}$C NMR (75 MHz, DMSO-$d_6$): δ 55.73, 36.95, 36.17, 34.09, 27.45, 12.87;

UV-Vis (water): 469, 317, 242 nm; and

Elemental analysis (calcd for $C_{24}H_{44}N_2MoS_4$):
Calculated: C, 49.29; H, 7.58; N, 4.79; S: 21.93.
Found: C, 49.34; H, 7.66; N, 4.81; S: 21.79.

Example 6

Bis(2-ammoniumadamantane)tetrathiomolybdate, [Formula (I), C]

A solution of ammonium tetrathiomolybdate (0.26 g, 0.98 mmol) in D.I.U.F. water (5.0 mL) was added dropwise at ambient temperature to a stirred solution of 2-amino-adamantane hydrochloride (0.38 g, 2.0 mmol) in D.I.U.F. water (2.0 mL). An orange solid formed. The suspension was stirred at RT for 0.5 h and under ice cooling (5° C., bath) for 1 h. The solids were filtered off, washed twice with ice cold D.I.U.F. water (10 mL each time) and dried in vacuum (1 mmHg) at 50° C. for 19.5 h to yield 0.51 g (98.4%) of title compound as an orange solid, m.p. 205° C. Its spectra are as follows:

$^1$H NMR (300 MHz, DMSO-$d_6$): δ 7.79 (br, 6H), 3.59 (br s, 2H), 1.98 (br s, 8H), 1.80 (m, 12H), 1.69 (br s, 4H), 1.55 (d, J=12.7 Hz, 4H);

$^{13}$C NMR (75 MHz, DMSO-$d_6$): δ 54.99, 36.78, 36.17, 30.08, 29.51, 26.41, 26.31;

UV-Vis (water): 469, 317, 242 nm; and

Elemental analysis (calcd for $C_{20}H_{36}N_2MoS_4 \cdot 0.4H_2O$):
Calculated: C, 44.83; H, 6.92; N, 5.23; S: 23.93.
Found: C, 44.68; H, 6.72; N, 5.41; S: 24.01.

Example 7

Bis(2-ammoniumadamantane)tetrathiotungstate, [Formula (I), C]

Ammonium tetrathiotungstate (0.35 g, 1.0 mmol) was suspended in D.I.U.F. water (10.0 mL) and stirred for 0.5 h. Small insoluble particles were filtered off. The filtrate was added dropwise at RT to a stirred solution of 2-adamantanamine hydrochloride (0.38 g, 2.0 mmol) in D.I.U.F. water (2.0 mL). A yellow solid formed. The suspension was stirred at RT for 0.5 h and under ice cooling (5° C., bath) for 1 h. The formed solids were filtered off, washed twice with ice cold D.I.U.F. water (1.0 mL each time) and dried in vacuum (1 mmHg) at 50° C. for 18.5 h to yield 0.5 g (81.1%) of title compound as a yellow solid, m.p. 245-250° C. Its spectra are as follows:

$^1$H NMR (300 MHz, DMSO-$d_6$): δ 7.76 (br, 6H), 3.59 (br, 2H), 1.98 (m, 8H), 1.80 (m, 12H), 1.69 (br s, 4H), 1.54 (d, J=12.7 Hz, 4H);

$^{13}$C NMR (75 MHz, DMSO-$d_6$): δ 54.93, 36.82, 36.22, 30.18, 29.53, 26.44, 26.33;

UV-Vis (water): 393, 334, 277, 215 nm; and

Elemental analysis (calcd for $C_{20}H_{36}N_2S_4W$):
Calculated: C, 38.96; H, 5.88; N, 4.54; S: 20.80.
Found: C, 39.13; H, 6.03; N, 4.59; S: 16.11.

(Note: The elemental analysis for sulfur did not fit the calculated formula. A possible explanation for this result is that the sulfur was partially exchanged for oxygen under the reaction conditions, which are unoptimized.)

Example 8

Bis(1-ammonium-3,5-dimethyladamantane)tetrathiotungstate, [Formula (I), A]

Ammonium tetrathiotungstate (0.35 g, 1.0 mmol) was suspended in D.I.U.F. water (10.0 mL) and stirred for 0.5 h. Small insoluble particles were filtered off. Memantine hydrochloride (0.43 g, 2.0 mmol) was added to the filtrate. The suspension was stirred at RT for 0.5 h and under ice cooling (5° C., bath) for 1 h. A yellow solid formed, which was filtered off, washed twice with ice cold D.I.U.F. water (1.0 mL each time) and dried in vacuum (1 mmHg) at 50° C. for 17 h to yield 0.53 g (78.8%) of title compound as a yellow solid, m.p. 209-211° C. Its spectra are as follows:

$^1$H NMR (300 MHz, DMSO-$d_6$): δ 7.70 (br, 6H), 2.14 (br s, 2H), 1.63 (br s, 4H), 1.46, 1.39 (AB-system, J=11.4 Hz, 8H), 1.29 (br s, 8H), 1.15, 1.09 (AB-system, J=12.8 Hz, 4H), 0.85 (s, 12H);

$^{13}$C NMR (75 MHz, DMSO-$d_6$): δ 52.23, 49.43, 45.98, 41.45, 38.59, 32.01, 29.64, 29.17;

UV-Vis (water): 393, 334, 277, 216 nm; and

Elemental analysis (calcd for $C_{24}H_{44}N_2S_4W$):
Calculated: C, 42.85; H, 6.59; N, 4.16; S: 19.06.
Found: C, 42.80; H, 6.74; N, 4.26; S: 14.28.

(Note: The elemental analysis for sulfur did not fit the calculated formula. A possible explanation for this result is that the sulfur was partially exchanged for oxygen under the reaction conditions, which are unoptimized.)

Although the invention has been described with reference to its preferred embodiments, those of ordinary skill in the art may, upon reading and understanding this disclosure, appreciate changes and modifications which may be made which do not depart from the scope and spirit of the invention as described above or claimed hereafter.

What is claimed is:

1. A compound of the formula $$Z^+ \cdot M^{2-} \cdot Z^+ \qquad \text{Formula (I)}$$

wherein:

$M^{2-}$ is selected from the group consisting of $MoO_3S^{2-}$, $MoO_2S_2^{2-}$, $MoOS_3^{2-}$, $MoS_4^{2-}$, $[MO_2(S_2)_6]^{2-}$, $[Mo_2S_4(S_2)_2]^{2-}$, $[Mo_2S_4(S_4)_2]^{2-}$, $[Mo_3S(S_2)_6]^{2-}$, $WO_3S^{2-}$, $WO_2S_2^{2-}$, $WOS_3^{2-}$ and $WS_4^{2-}$;

$Z^+$ is joined to $M^{2-}$, as shown by the dot, ionically;

$Z^+$ is independently an organic ammonium moiety with an alicyclic or a polyalicyclic group of the tricyclic adamantane selected from the group as shown by Formulae (A), (B) and (C) or monoalicyclic neramexane type as shown by Formula (D), respectively,

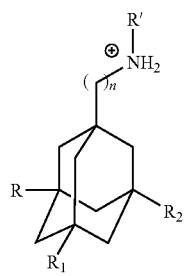

Formula (A)

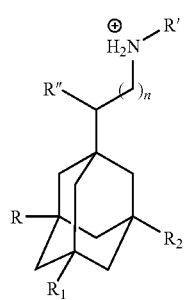

Formula (B)

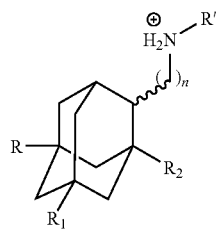

Formula (C)

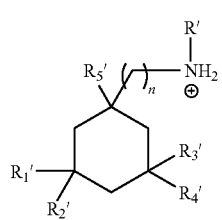

Formula (D)

wherein:

in Formula (A):

R, $R_1$ and $R_2$ are each independently H or $C_1$-$C_6$ straight- or branched-chain alkyl, $C_3$-$C_7$ cycloalkyl, $C_1$-$C_6$ straight- or branched-chain fluoroalkyl, $C_2$-$C_6$ alkenyl, $C_2$-$C_6$ alkynyl, alkoxyl, t-butoxycarbonyl, t-butoxycarbonylmethyl, hydroxy, hydroxymethyl, alkoxymethyl, azido, cyano, halo, nitro, trihaloalkyl, $C_1$-$C_6$ mercaptoalkyl, $C_6$-$C_{10}$, alkyl($C_6$-$C_{10}$ aryl), and alkyldiaryl;

n=0, 1 or 2; and

R' is H or $C_1$-$C_4$ straight- or branched-chain alkyl, or $C_3$-$C_7$ cycloalkyl;

in Formula (B):

R, $R_1$ and $R_2$ are each independently H or $C_1$-$C_6$ straight- or branched-chain alkyl, $C_3$-$C_7$ cycloalkyl, $C_1$-$C_6$ straight- or branched-chain fluoroalkyl, $C_2$-$C_6$ alkenyl, $C_2$-$C_6$ alkynyl, alkoxyl, t-butoxycarbonyl, t-butoxycarbonylmethyl, hydroxy, hydroxymethyl, alkoxymethyl, azido, cyano, halo, nitro, trihaloalkyl, $C_1$-$C_6$ mercaptoalkyl, $C_6$-$C_{10}$ aryl, alkyl ($C_6$-$C_{10}$) aryl, and alkyldiaryl;

n=0, 1 or 2;

R' is H or $C_1$-$C_4$ straight- or branched-chain alkyl, or $C_3$-$C_7$ cycloalkyl; and R" is $C_1$-$C_4$ straight- or branched-chain alkyl, or $C_3$-$C_7$ cycloalkyl;

in Formula (C):

R, $R_1$ and $R_2$ are each independently H or $C_1$-$C_6$ straight- or branched-chain alkyl, $C_3$-$C_7$ cycloalkyl, $C_1$-$C_6$ straight- or branched-chain fluoroalkyls, $C_2$-$C_6$ alkenyl, $C_2$-$C_6$ alkynyl, alkoxyl, t-butoxycarbonyl, t-butoxycarbonylmethyl, hydroxy, hydroxymethyl, alkoxymethyl, azido, cyano, halo, nitro, trihaloalkyl, $C_6$-$C_{10}$ aryl, alkyl ($C_6$-$C_{10}$) aryl, alkyldiaryl unsubstituted or substituted with one or more $C_1$-$C_6$ straight- or branched-chain alkyl, $C_1$-$C_6$ alkoxyl, 1,3-dioxolanyl or trihaloalkyl;

n=0, 1 or 2;

R' is H or $C_1$-$C_4$ straight- or branched-chain alkyl, or $C_3$-$C_7$ cycloalkyl; and in Formula (D):

$R_1'$, $R_2'$, $R_3'$, $R_4'$ and $R_5'$ are each independently, $C_1$-$C_6$ straight-chain alkyl, or branched-chain alkyl, $C_3$-$C_7$ cycloalkyls, $C_1$-$C_6$ straight- or branched-chain fluoroalkyls, $C_2$-$C_6$ alkenyl, $C_2$-$C_6$ alkynyl, alkoxyl, t-butoxycarbonyl, t-butoxycarbonylmethyl, halo, hydroxy, hydroxymethyl, alkoxymethyl, trihaloalkyl, $C_6$-$C_{10}$ aryl, alkyl ($C_6$-$C_{10}$) aryl, and alkyldiaryl, unsubstituted or substituted with one or more $C_1$-$C_6$ straight- or branched-chain alkyl, $C_1$-$C_6$ alkoxyl, 1,3-dioxolanyl or trihaloalkyl;

$R_5'$ is also independently H;

$R_1'$ and $R_2'$ may be optionally tethered together to form 3- to 7-membered alicyclic ring;

$R_3'$, and $R_4'$ may be optionally tethered together to form 3- to 7-membered alicyclic ring;

n=0, 1 or 2; and

R' is H or $C_1$-$C_4$ straight- or branched-chain alkyl, or $C_3$-$C_7$ cycloalkyl.

2. The compound of claim 1 where in Formula (I) A:

$M^{2-}$ is $MoS_4^{2-}$ or $WS_4^{2-}$;

$Z^+$ is an organic ammonium moiety of the tricyclic adamantane type as shown by Formula (A) wherein:

R, $R_1$ and $R_2$ are each independently H or $C_1$-$C_6$ straight- or branched-chain alkyl, $C_3$-$C_7$ cycloalkyl, $C_1$-$C_6$ straight- or branched-chain fluoroalkyls, $C_2$-$C_6$ alkenyl, $C_2$-$C_6$ alkynyl, alkoxyl, t-butoxycarbonyl, t-butoxycarbonylmethyl, hydroxy, hydroxymethyl, alkoxymethyl, azido, cyano, halo, nitro, trihaloalkyl, $C_1$-$C_6$ mercaptoalkyl, $C_6$-$C_{10}$ aryl, alkyl ($C_6$-$C_{10}$)aryl, and alkyldiaryls, unsubstituted or substituted with one or more $C_1$-$C_6$ straight- or branched-chain alkyls, $C_1$-$C_6$ alkoxyl, 1,3-dioxolanyl or trihaloalkyl;

n=0, 1 or 2; and

R' is H or $C_1$-$C_4$ straight- or branched-chain alkyl, or $C_3$-$C_7$ cycloalkyl.

3. The compound of claim 1 where in Formula (I) A:

$M^{2-}$ is $MoS_4^{2-}$ or $WS_4^{2-}$;

$Z^+$ is an organic ammonium moiety of the tricyclic adamantane type as shown by Formula (A) wherein:

R and R' are H;

$R_1$ and $R_2$ are H, methyl or ethyl; and n=0, 1 or 2.

4. The compound of claim 1 where in Formula (I) B:

$M^{2-}$ is $MoS_4^{2-}$ or $WS_4^{2-}$;

$Z^+$ is an organic ammonium moiety of the tricyclic adamantane type as shown by Formula (B) wherein:

R, $R_1$ and $R_2$ are each independently H or $C_1$-$C_6$ straight- or branched-chain alkyl, $C_3$-$C_7$ cycloalkyl, $C_1$-$C_6$ straight- or branched-chain fluoroalkyls, $C_2$-$C_6$ alkenyl, $C_2$-$C_6$ alkynyl, alkoxyl, t-butoxycarbonyl, t-butoxycarbonylmethyl, hydroxy, hydroxymethyl, alkoxymethyl, azido, cyano, halo, nitro, trihaloalkyl, $C_1$-$C_6$ mercaptoalkyl, $C_6$-$C_{10}$ aryl, alkyl ($C_6$-$C_{10}$)aryl, and alkyldiaryls, unsubstituted or substituted with $C_1$-$C_6$ straight- or branched-chain alkyls, $C_1$-$C_6$ alkoxyl, 1,3-dioxolanyl or trihaloalkyl;

n=0, 1 or 2;

R' is H or $C_1$-$C_4$ straight- or branched-chain alkyl, or $C_3$-$C_7$ cycloalkyl; and R" is $C_1$-$C_4$ straight- or branched-chain alkyl, or $C_3$-$C_7$ cycloalkyl.

5. The compound of claim 1 where in Formula (I) B:

$M^{2-}$ is $MoS_4^{2-}$ or $WS_4^{2-}$;

$Z^+$ is an organic ammonium moiety of the tricyclic adamantine type as shown by Formula (B) wherein:

R and R' are H;

$R_1$ and $R_2$ are H, methyl or ethyl;

n=0, 1 or 2; and

R" is methyl or ethyl.

6. The compound of claim 1 where in Formula (I) C:

$M^{2-}$ is $MoS_4^{2-}$ or $WS_4^{2-}$;

$Z^+$ is an organic ammonium moiety of the tricyclic adamantane type as shown by Formula (C) wherein:

R, $R_1$ and $R_2$ are each independently H or $C_1$-$C_6$ straight- or branched-chain alkyl, $C_3$-$C_7$ cycloalkyl, $C_1$-$C_6$ straight- or branched-chain fluoroalkyls, $C_2$-$C_6$ alkenyl, $C_2$-$C_6$ alkynyl, alkoxyl, t-butoxycarbonyl, t-butoxycarbonylmethyl, hydroxy, hydroxymethyl, alkoxymethyl, azido, cyano, halo, nitro, trihaloalkyl, $C_1$-$C_6$ mercaptoalkyl, $C_6$-$C_{10}$ aryl, alkyl ($C_6$-$C_{10}$)aryl, and alkyldiaryls, unsubstituted or substituted with $C_1$-$C_6$ straight- or branched-chain alkyls, $C_1$-$C_6$ alkoxyl, 1,3-dioxolanyl or trihaloalkyl;

n=0, 1 or 2; and

R' is H or $C_1$-$C_4$ straight- or branched-chain alkyl, or $C_3$-$C_7$ cycloalkyl.

7. The compound of claim 1 where in Formula (I) C:

$M^{2-}$ is $MoS_4^{2-}$ or $WS_4^2$;

$Z^-$ is an organic ammonium moiety of the tricyclic adamantane type as shown by Formula (C) wherein:

R and R' are H;

$R_1$ and $R_2$ are H, methyl or ethyl;

n=0, 1 or 2.

8. The compound of claim 1 where in Formula (I) D:

$M^{2-}$ is $MoS_4^{2-}$ or $WS_4^{2-}$;

$Z^+$ is an organic ammonium moiety of the monoalicyclic neramexane type as shown by Formula (D) wherein:

$R_1'$, $R_2'$, $R_3'$, $R_4'$ and $R_5'$ are each independently, $C_1$-$C_6$ straight-chain or branched-chain alkyl, $C_3$-$C_7$ cycloalkyl, $C_1$-$C_6$ straight- or branched-chain fluoroalkyl, $C_2$-$C_6$ alkenyl, $C_2$-$C_6$ alkynyl, alkoxyl, t-butoxycarbonyl, t-butoxycarbonylmethyl, halo, hydroxy, hydroxymethyl, alkoxymethyl, trihaloalkyl, $C_6$-$C_{10}$ aryl, alkyl ($C_6$-$C_{10}$) aryl, and alkyldiaryls, unsubstituted or substituted with $C_1$-$C_6$ straight- or branched-chain alkyls, $C_1$-$C_6$ alkoxyl, 1,3-dioxolanyl or trihaloalkyl;

$R_5'$ is also independently H;

$R_1'$ and $R_2'$ may be optionally tethered together to form 3- to 7-membered alicyclic ring;

$R_3'$ and $R_4'$ may be optionally tethered together to form 3- to 7-membered alicyclic ring;

n=0, 1 or 2; and

R' is H or $C_1$-$C_4$ straight- or branched-chain alkyl, or $C_3$-$C_7$ cycloalkyl.

9. The compound of claim 1 where in Formula (I) D:

$M^{2-}$ is $MoS_4^{2-}$ or $WS_4^{2-}$;

$Z^+$ is an organic ammonium moiety of the monoalicyclic neramexane type as shown by Formula (D) wherein:

$R_1'$, $R_2'$, $R_3'$, and $R_4'$ are each independently methyl or ethyl;

$R_5'$ is H, methyl or ethyl;

n=0, 1 or 2; and

R' is H.

10. The following compound, as its tetrathiomolybdate ($MoS_4^{2-}$) or tetrathiotungstate ($WS_4^{2-}$) salt, 3,6-dimethyl-9-(2-methylpyridyl-5)ethyl-1,2,3,4-tetrahydro-γ-carboline.

11. The compound of any one of claims 1 to 10 wherein the compound is a hydrate, a solvate, stereoisomer or mixtures of stereoisomers, enantiomers or diasteroisomers.

12. The compound of Formula (I) as defined in claim 1, wherein $M^{2-}$ is $MoS_4^{2-}$ or $WS_4^2$; and $Z^+$ is as defined in claim 1.

13. Bis(1-ammonium-3,5-dimethyladamantane) tetrathiomolybdate, or as its solvate with dimethylsulfoxide as a stable crystalline form.

14. A pharmaceutical formulation comprising at least one of the compounds of Formula (I) as defined in claim 1 or 13 as an active substance and a pharmaceutically-acceptable carrier.

15. The pharmaceutical formulation of claim 14 wherein the formulation is in a form of: tablets; capsules; solutions, suspensions, syrups and elixirs; long acting, slow release depot forms made up of granules, liposomes, ointments, or patches; injections for intravenous, intramuscular subcutaneous, or intraperitoneal, administration; solid nanodispersions for oral or intranasal delivery; topical ophthalmic; and suppositories for vaginal or rectal administration.

16. The pharmaceutical formulation of claim 14 wherein the active substance is present in an effective amount in a single dose or multiple doses.

17. A composition comprising the compounds of any one of claims 1-10 for the treatment, in humans or animals in need of such treatment, of dementia of Alzheimer's disease, or other dementias; viral infections; Wilson's disease; and diseases of the eye, wherein the compound is present in an effective amount in a single dose or multiple doses in a pharmaceutically-acceptable formulation.

18. A method for treating neurodegenerative diseases by use of a therapeutically effective amount of the pharmaceutical formulation of claim 14 administered to an animal or human in need of such treatment.

19. The method of claim of claim 18 wherein the formulation is used in combination with an acetylcholinesterase (AChE) inhibitor.

20. The method of claim 19 wherein the acetylcholinesterase (AChE) inhibitor is donepezil, rivastigmine, tacrine or galanthamine.

21. The method of claim 18 where the disease is treatment of dementia of Alzheimer's disease, Parkinson's, Huntington's and AIDS-related dementia, schizophrenia and its cognitive deficits.

22. The method of claim 18 wherein the pharmaceutical formulation is administered in a form of: tablets; capsules; solutions, suspensions, syrups and elixirs; long acting, slow release depot forms made up of granules, liposomes, ointments, or patches; injections for intravenous, intramuscular subcutaneous, or intraperitoneal, administration; solid nanodispersions for oral or intranasal delivery; topical ophthalmic; and suppositories for vaginal or rectal administration.

23. The method of administering therapeutically effective amount of the pharmaceutical formulation of claim 14 as medicinal agents for treating animals and humans, in need of such treatment of neurodegenerative diseases.

24. The method according to claim 23 wherein the neurodegenerative disease is dementia of Alzheimer's disease, Parkinson's, Huntington's and AIDS-related dementia, schizophrenia and its cognitive deficits; viral infections; and neurologically presenting Wilson's disease; and diseases of the eye such as proliferative diabetic retinopathy, age related macular degeneration and glaucoma.

25. The compound of claim 1 (A) or claim 1 (B) wherein $C_6$-$C_{10}$ aryl is selected from the group consisting of phenyl, unsubstituted or substituted with one or more $C_1$-$C_6$ straight- or branched-chain alkyl, $C_1$-$C_6$ alkoxyl, t-butoxycarbonyl, hydroxy, azido, halo, nitro, trihaloalkyl, or $C_1$-$C_6$ mercaptoalkyl; and alkyl($C_6$-$C_{10}$aryl) is selected from the group consisting of a benzyl group, unsubstituted or substituted with one or more $C_1$-$C_6$ straight- or branched-chain alkyl, $C_1$-$C_6$ alkoxyl, 1,3-dioxolanyl, t-butoxycarbonyl, hydroxy, azido, halo, and or trihaloalkyl; and alkyldiaryl selected from the group consisting of diphenylmethyl, unsubstituted or substituted with one or more $C_1$-$C_6$ straight- or branched-chain alkyl, $C_1$-$C_6$ alkoxyl, 1,3-dioxolanyl, halo, and trihaloalkyl.

26. The compound of claim 1 (C) wherein $C_6$-$C_{10}$ aryl is selected from the group consisting of phenyl, unsubstituted or substituted with one or more $C_1$-$C_6$ straight- or branched-chain alkyl, $C_1$-$C_6$ alkoxyl, t-butoxycarbonyl, hydroxy, azido, halo, nitro, and trihaloalkyl; and alkyl ($C_6$-$C_{10}$) aryl is selected from the group consisting of a benzyl group, unsubstituted or substituted with one or more $C_1$-$C_6$ straight- or branched-chain alkyl, $C_1$-$C_6$ alkoxyl, 1,3-dioxolanyl, t-butoxycarbonyl, hydroxy, azido, halo, and trihaloalkyl; and alkyldiaryls are diphenylmethyl.

27. The compound of claim 1 (D) wherein $C_6$-$C_{10}$ aryl is selected from the group consisting of phenyl, unsubstituted or substituted with one or more $C_1$-$C_6$ straight- or branched-chain alkyl, $C_1$-$C_6$ alkoxyl, t-butoxycarbonyl, halo, hydroxy, and trihaloalkyl; and alkyl ($C_6$-$C_{10}$) aryl selected from the group consisting of a benzyl group, unsubstituted or substituted with one or more $C_1$-$C_6$ straight- or branched-chain alkyl, $C_1$-$C_6$ alkoxyl, 1,3-dioxolanyl, t-butoxycarbonyl, halo, hydroxy, azido, and trihaloalkyl; and alkyldiaryl is diphenylmethyl.

28. The compound of any one of claim 2, 4, 6 or 8 wherein $C_6$-$C_{10}$ aryl is selected from the group consisting of phenyl, unsubstituted or substituted with one or more $C_1$-$C_6$ straight-chain or branched-chain alkyl, $C_1$-$C_6$ alkoxyl, t-butoxycarbonyl, hydroxy, azido, halo, nitro, trihaloalkyl or $C_1$-$C_6$ mercaptoalkyl; and alkyl ($C_6$-$C_{10}$)aryl is selected from the group consisting of a benzyl group, unsubstituted or substituted with one or more $C_1$-$C_6$ straight- or branched-chain alkyl, $C_1$-$C_6$ alkoxyl, 1,3-dioxolanyl, t-butoxycarbonyl, hydroxy, azido, halo, and trihaloalkyl.

29. The composition of claim 17 wherein the other dementias are Parkinson's, Huntington's and AIDS-related dementia, and schizophrenia and its cognitive deficits.

30. The composition of claim 17 wherein diseases of the eye are retinopathy, proliferative diabetic retinopathy, age related macular degeneration, and glaucoma.

* * * * *